United States Patent [19]
Behr et al.

[11] Patent Number: 5,545,414
[45] Date of Patent: Aug. 13, 1996

[54] CHOLESTEROL LOWERING FOOD PRODUCT

[75] Inventors: Stephen R. Behr, Westerville; Jeffrey K. Seeds, Pickerington; Catherine S. Lamb, Westerville; Keith A. Garleb, Powell; Joseph E. Walton, Westerville, all of Ohio

[73] Assignee: Abbott Laboratories, Abbott Park, Ill.

[21] Appl. No.: 408,467

[22] Filed: Mar. 22, 1995

[51] Int. Cl.$^6$ .............. A61K 9/32; A61K 9/14; A61K 9/16; A61K 9/50

[52] U.S. Cl. .......... 424/484; 424/485; 424/488; 424/490; 424/491; 424/493; 424/499; 514/824

[58] Field of Search .................. 424/439, 469, 424/485, 484, 488, 490, 491, 493, 499, 502; 514/824

[56] References Cited

U.S. PATENT DOCUMENTS

| | | | |
|---|---|---|---|
| 3,089,824 | 5/1963 | Wurster | 424/489 |
| 3,117,027 | 1/1964 | Lindlof et al. | 118/303 |
| 3,196,827 | 7/1965 | Wurster et al. | 416/39 |
| 3,241,520 | 3/1966 | Wurster et al. | 118/62 |
| 3,253,944 | 5/1966 | Wurster | 427/213 |
| 4,384,004 | 5/1983 | Cea et al. | 426/3 |
| 4,496,606 | 1/1985 | Michnowski | 426/658 |
| 4,882,160 | 11/1989 | Yang et al. | 424/440 |
| 4,927,649 | 5/1990 | Antenucci | 426/273 |

OTHER PUBLICATIONS

Bucolo, Clinical Chemistry, 19(5):476–482 (1973).
Allain et al., Clinical Chemistry, 20(4)470–481 (1974).
Jenkins et al., The Lancet, May (1975), pp. 1116–1117.
Haber et al., The Lancet Oct. 1, 1977, pp. 679–682.
Sirtori et al., The Lancet, Feb. 5, 1977, pp. 275–277.
Huff et al., Atherosclerosis, 28;187–195 (1977).
Kay et al., The American Journal of Clinical Nutrition, 30:171–175 (1977).
Kelley et al., Journal of Nutrition, 108:630–639.
Turley et al., Journal of Lipid Research, 19:924–928 (1978).
Sirtori et al., The American Journal of Clinical Nutrition, 32:1645–1658 (1979).
Chen et al., Journal of Nutrition, 109:1028–1034 (1979).
Reddy et al., Journal of Nutrition, 110:1247–1254 (1980).
Pfeffer et al., Journal of Agricultural Food Chemistry, 29:455–461 (1981).
Mattson et al., The American Journal of Clinical Nutrition, 35:697–700 (1982).
Journal of the American Medical Association, 251(3):351–364 (1984).
Journal of the American Medical Association, 251(3):365–374 (1984).
Chen et al., Proceedings of the Society of Experimental Biology and Medicine, 175:215–218 (1984).
Qureshi et al., The Journal of Biological Chemistry, 261(23):10544–10550 (1986).
Ahrens et al., Journal of Nutrition, 116:70–76 (1986).
Jenkins et al., Handbook of Dietary Fiber in Nutrition, CRC Press, (1986) pp. 327–344.
Vigne et al., British Journal of Nutrition, 58:405–413 (1987).
Kannel, American Heart Journal, 114:213–219 (1987).
Archives of Internal Medicine, 148:36–69 (1988).
Sugano et al., Dietary Fiber, Chemistry, Physiology and Health Effects, Plenum Press (1988), pp. 137–155.
Grundy et al., American Journal of Clinical Nutrition, 47:965–969 (1988).
Matthews et al., The New England Journal of Medicine, 321(10):641–646 (1989).
Circulation, 77(3):721A–724A (1988).
Banks et al., Journal of the National Medical Association, 81(5):493–495 (1989).
Meinertz et al., American Journal of Clinical Nutrition, 50:786–793 (1989).
Koseki et al., Agricultural Biological Chemistry, 53(12):3127–3132 (1989).
Nishima et al., Journal of Nutrition, 120:668–673 (1990).
Anderson et al., Critical Reviews in Food Science and Nutrition, 29(2):95–147 (1990).
Carroll, Journal of the American Dietetic Association, 91(7):820–827 (1991).
Ide et al., Annals of Nutrition and Metabolism, 35:34–44 (1991).
Nicolosi et al., Arteriosclerosis, 11:1603a (1991).
Nicolosi et al., Atherosclerosis, 88:133–142 (1991).
Evans et al., British Journal of Nutrition, 68:217–229 (1992).
Fernandez et al., Journal of Nutrition, 122:2330–2340 (1992).
Journal of the American Medical Association, 269(23):3015–3023 (1993).
Ebihara et al., Nutrition Research, 13:209–217 (1993).
Remesy et al., American Journal of Physiology, 264:G855–G862 (1993).
Gallaher et al., Journal of Nutrition, 123:244–252 (1993).
Riottot et al., Lipids, 28:181–188 (1993).
Flourie et al., Journal of Nutrition, 123:676–680 (1993).
Levrat et al., Journal of Nutrition, 124(4):531–538 (1994).
Lichtenstein et al., Arteriosclerosis and Thrombosis, 14(4):549–546 (1994).
Jones et al., Arteriosclerosis and Thrombosis, 14(4):542–548 (1994).
Merck Index, 9th ed. 1976, p. 1366 #9779.

*Primary Examiner*—John W. Rollins
*Attorney, Agent, or Firm*—Lonnie R. Drayer; Thomas D. Brainard

[57] ABSTRACT

A nutritional product having a solid matrix containing protein, fat and carbohydrate has disposed therein particles of dietary fiber encapsulated in zein. The preferred dietary fiber is guar. Such a nutritional product may be used for reducing the serum cholesterol in a mammal.

19 Claims, No Drawings

CHOLESTEROL LOWERING FOOD PRODUCT

The present invention relates to a nutritional product with a solid matrix containing encapsulated dietary fiber, which reduces serum cholesterol in mammals.

Atherosclerosis is a disease of the arteries which begins as a lipid filled lesion in the intima of the arterial wall and progresses gradually with the eventual formation of a fibroatheromatous plaque over a period of years. The disease often affects the coronary arteries which perfuse the heart. Once significant encroachment on the vessel lumen occurs, coronary flow may be insufficient to meet myocardial oxygen demands, causing thoracic pain (stable angina pectoris). Eventually, the plaque may fissure or rupture, with or without overlying thrombosis. Plaque disruption may cause an abrupt reduction in coronary perfusion, leading to unstable angina, myocardial infarction (necrosis of the heart muscle resulting from interruption of the blood supply to the area) or ischemic sudden death, presumably due to ventricular arrhythmia. Heart disease can be the result of several etiologies, but it is most often due to atherosclerotic obstruction of large coronary arteries. More than half the deaths related to heart disease can be attributed to atherosclerosis.

The risk factor hypothesis of atherosclerosis has become well accepted in the medical world: the majority of people who die or are disabled as a result of atherosclerosis exhibit one or more identifiable characteristics called risk factors. If a person has a risk factor, he or she is more likely to develop clinical manifestations of atherosclerosis and is likely to do so earlier than is a person with no risk factors. The following parameters have been shown to be associated with coronary heart disease (CHD) in the Framingham study and other large epidemiological studies and are now well accepted: age (the relation of age to CHD is also dependent on sex) and family history of premature CHD, hypercholesterolemia and specifically high blood levels of low density lipoprotein (LDL) cholesterol, low levels of high density lipoprotein (HDL) cholesterol, cigarette smoking, hypertension, and diabetes each contributes to increasing the risk of disease over baseline rates by a factor of 2 to 6-fold. When these characteristics are combined, the combined risks of coronary heart disease are additive (Dauber, "The Epidemiology of Atherosclerotic Disease", THE HARVARD UNIVERSITY PRESS, 1980; Kannel, "New Perspectives on Cardiovascular Risk Factors", AMERICAN HEART JOURNAL, 114:213–219, 1987; Matthews et al., "Menopause and Risk Factors for Coronary Heart Disease", THE NEW ENGLAND JOURNAL OF MEDICINE, 321(10):641–646, 1989; "Report of the National Cholesterol Education Program Expert Panel on detection, evaluation, and treatment of high blood cholesterol in adults", ARCHIVES OF INTERNAL MEDICINE, 148:36–69, 1988)

Just as important as the identification of cholesterol as a risk factor is the fact that when blood cholesterol and specifically LDL cholesterol levels are decreased in hypercholesterolemic subjects, there is a decrease in risk of heart disease. The results of the Lipid Research Clinic trials indicate that for every percentage point decrease in cholesterol levels, the risk of coronary heart disease decreases by 2%. ("Lipid Research Clinics Program. The Lipid Research Clinics Primary Prevention Trial Results I. Reduction in incidence of coronary heart disease", JOURNAL OF THE AMERICAN MEDICAL ASSOCIATION, 251(3)351–364, 1984; "Lipid Research Clinics Program. The Lipid Research Clinics Coronary Primary Prevention Results II. The relationship of reduction in incidence of coronary heart disease to cholesterol lowering", JOURNAL OF THE AMERICAN MEDICAL ASSOCIATION, 251(3)365–374, 1984)

The blood cholesterol raising effects of dietary saturated fat and cholesterol are well accepted. Therefore, the American Heart Association and the National Cholesterol Education Program recommend as their "Step 1" diet a cholesterol-lowering program consisting of a reduction of total fat to less than 30% of calories as fat, a reduction of saturated fatty acids to less than 10% of calories and a reduction of cholesterol to less than 300 mg per day. It is also accepted that polyunsaturated fat lowers blood cholesterol, but because of the relatively small amount of data on the long term use of diets with very high polyunsaturated fat content, the American Heart Association and the National Academy of Sciences do not recommend that polyunsaturates exceed 10% of calories. (Expert Panel, "Summary of the Second Report of the National Cholesterol Education Program (NCEP) Expert Panel on Detection, Evaluation and Treatment of High Blood Cholesterol in Adults (Adult Treatment Panel II)", JOURNAL OF THE AMERICAN MEDICAL ASSOCIATION, 269(23):3015–3023, 1993; Nutrition Committee of the American Heart Association, "Dietary Guidelines for Healthy American Adults", CIRCULATION, 77(3):721A–724A, 1988; Food and Nutrition Board, National Research Council, RECOMMENDED DIETARY ALLOWANCES, 10TH EDITION, National Academy Press, Washington, D.C., 1989). The National Cholesterol Education Program guidelines also state that monounsaturates should make up 10–15% of the diet, protein 10–20%, carbohydrate 50–60%, and dietary fiber 15–25 g/day. The type of dietary fiber is not specified.

For people who are eating an average American diet, switching to a Step 1 diet means decreasing their intake of fat. In the Multiple Risk Factor Intervention Trial, dietary changes according to a Step 1 diet were initiated leading to decreases in serum cholesterol in the range of 5–7%. (Banks et al., "Dietary Management of the Patient with Atherosclerosis: Are the New National Cholesterol Education Panel Recommendations Enough?", JOURNAL OF THE NATIONAL MEDICAL ASSOCIATION, 81(5):493–495, 1989). That means that if the ultimate goal is to reduce total cholesterol levels to less than 200 mg/dL, individuals who are consuming an average American diet and have serum cholesterol levels over 215–220 mg/dL will need to rely on more than a Step 1 diet.

A more stringent dietary recommendation of the National Cholesterol Education Program is the "Step 2 diet" which further restricts saturated fat to 7% of calories and cholesterol to less than 200 mg per day. One drawback of the Step 2 diet and other very low fat diets in that in addition to lowering LDL they lower HDL. (Jones et al., "Effect of dietary fat selection on plasma cholesterol synthesis in older, moderately hypercholesterolemic humans", ARTERIOSCLEROSIS AND THROMBOSIS, 14(4):542–548, 1994; Grundy et al., "Comparison of monounsaturated fatty acids and carbohydrates for reducing raised levels of plasma cholesterol in man", AMERICAN JOURNAL OF CLINICAL NUTRITION, 47:965–969, 1988)

The Step 1 diet does not provide specific recommendations for any other components of the diet which might enhance its cholesterol-lowering or antiatherogenic potential. Additional cholesterol-lowering components include vegetable oils that contain non-saponifiable components, cholesterol-lowering dietary fibers, and vegetable proteins. Rice bran oil contains a sizeable unsaponifiable fraction, i.e., non-acyl glycerol portion that contains 2 general classes of compounds: (a) sterols, and triterpene alcohols and (b)

tocotrienols, which are similar to tocopherols, but with 3 double bonds in the side chain. The sterols and triterpene alcohols in rice bran oil are often esterified to ferulic acid and are known as "oryzanols". Studies in rats, primates and humans indicate that rice bran oil lowers serum cholesterol and may lower serum triglycerides. (Nicolosi, et al., "Rice bran oil lowers serum total and low density lipoprotein cholesterol and Apo B levels in nonhuman primates", ATHEROSCLEROSIS, 88:133–142, 1991; Lichenstein et al., "Rice bran oil consumption and plasma lipid levels in moderately hypercholesterolemic humans", ARTERIOSCLEROSIS AND THROMBOSIS, 14(4):549–546, 1994) Two different mechanisms may be involved. First, plant sterols and oryzanols may interfere with cholesterol or saturated fat absorption and/or the absorption of bile acids. Second, in studies in chicks, pigs, and quail, tocotrienols have been reported to reduce cholesterol synthesis in the liver. It is also possible that plant sterols may prevent atherosclerosis by other mechanisms. (Mattson et al., "Optimizing the Effect of Plant Sterols on Cholesterol Absorption in Man", THE AMERICAN JOURNAL OF CLINICAL NUTRITION, 35:697–700, 1982; Qureshi et al., "The Structure of an Inhibitior of Cholesterol Biosynthesis Isolated from Barley", THE JOURNAL OF BIOLOGICAL CHEMISTRY, 261(23):10544–10550, 1986)

The cholesterol-lowering effects of dietary fiber have been summarized in several recent reviews. (Jenkins et al., "Fiber in the treatment of hyperlipidemia", *Handbook of Dietary Fiber in Nutrition*, G. Spiller, Ed., CRC Press, 1986 pp. 327–344; Sugano et al., "Dietary Fiber and Lipid Absorption", *Dietary Fiber: Chemistry, Physiology, and Health Effects*, Kritchevsky et al., Ed. Plenum Press, 1988 pp. 137–155; Anderson et al., "Dietary Fiber and Coronary Heart Disease", CRITICAL REVIEWS IN FOOD SCIENCE AND NUTRITION, 29(2):95–147, 1990. Viscous soluble fibers are effective cholesterol-lowering agents when compared to non-viscous insoluble fibers or digestible carbohydrates, but the effect is variable. Table 1 summarizes data from over 50 studies of human subjects. As indicated in Table 1, one can expect a decrease in serum cholesterol in the range of 10% to 15% with doses of an appropriate source of fiber ranging from 6 g/day to 50 g/day. The variability of the response could be due to differences in the dose, timing of administration, types of subjects enrolled, and purities and chemical compositions of the fiber sources. In general, guar gum has advantages over the other fibers listed in Table 1 as it is more consistently high level of dietary fiber than pectin, more readily available at higher quality than psyllium, and much more consistently effective than oat and soy products.

TABLE 1

CHOLESTEROL LOWERING EFFECT OF VARIOUS FIBER SOURCES

| Fiber Source | Total Cholesterol Mean decrease or range | LDL Cholesterol Mean decrease or range | Number of Studies |
|---|---|---|---|
| Guar Gum | −11.2% | −17% | 22 |
| Pectin | −12.4% | — | 14 |
| Psyllium | −13.1% | −20% (one study) | 10 |
| Soy Polysaccharide | −6.5% | — | 2 |
| Oat Products | −3 to −36% | 0 to −58% | 13 |

The most likely mechanisms for the cholesterol lowering effect of fiber according to Anderson et al., "Dietary fiber and coronary heart disease", CRITICAL REVIEWS IN FOOD SCIENCE AND NUTRITION, 29 (2):95–147, (1990) are: (1) modification of bile acid reabsorption in terminal ileum (interruption of the entero-hepatic cycle of bile acids); (2) interference with lipid absorption; and (3) down-regulation of the liver's capability to synthesize cholesterol.

Many soluble fibers are extensively or completely degraded by bacteria in the cecum, yet bile acids are not well reabsorbed once they are released from dietary fiber. This may be partly due to the products of fermentation. The production of short chain fatty acids (SCFA) causes a drop in colonic pH which may decrease the solubility and the passive reabsorption of bile acids. (Remesy et al., "Cecal fermentations in rats fed oligosaccharides (insulin) are modulated by dietary calcium levels", AMERICAN JOURNAL OF PHYSIOLOGY, 264:G855-G862, 1993)

Cholesterol biosynthesis in the liver is known to be regulated by intracellular cholesterol levels, but dietary fiber does not cause an increase in cholesterol biosynthesis in the liver that is commensurate with the requirements for bile acid synthesis. Several studies support the hypothesis that propionate generated by bacterial fermentation of fiber could exert a rate-controlling effect on liver cholesterol synthesis. (Chen et al., "Propionate may mediate the hypocholesterolemic effects of certain soluble plant fibers in cholesterol-fed rats", PROCEEDINGS OF THE SOCIETY OF EXPERIMENTAL BIOLOGY AND MEDICINE, 175:215–218, 1984; Ebihara et al., "Hypocholesterolemic effect of cecally infused propionic acid in rats fed a cholesterol-free, casein diet", NUTRITION RESEARCH, 13:209–217, 1993) Other data dispute the validity of this concept. (Evans et al., "Relationship between structure and function of dietary fibre: a comparative study of the effects of three galactomannans on cholesterol metabolism in the rat", BRITISH JOURNAL OF NUTRITION, 68:217–229, 1992; Nishina et al., "Effects of propionate on lipid biosynthesis in isolated rat hepatocytes", JOURNAL OF NUTRITION, 120:668–673, 1990)

Plant proteins such as soy protein appear to lower cholesterol. (Carroll, "Review of clinical studies on cholesterol-lowering response to soy protein", JOURNAL OF THE AMERICAN DIETETIC ASSOCIATION 91(7):820–827, 1991) Decreases of LDL cholesterol in the range of 15% to 20% relative to control diets containing primarily casein have been documented. (Meinertz et al., "Soy protein and casein in cholesterol-enriched diets: effects on plasma lipoproteins in normolipidemic subjects", THE AMERICAN JOURNAL OF CLINICAL NUTRITION, 50:786–793, 1989; Sirtori et al., "Clinical experience with the soybean protein diet in the treatment of hypercholesterolemia", THE AMERICAN JOURNAL OF CLINICAL NUTRITION, 32:1645–1658, 1979; Sirtori et al., "Soybean-protein diet in the treatment of type II hyperlipoproteinemia", THE LANCET, Feb. 5, 1977, pp. 275–277). The cholesterol lowering effect of soy protein has not been consistently observed in all subjects, and may be more pronounced in younger subjects and in hyperlipidemic subjects. (Meinertz et al., "Soy protein and casein in cholesterol-enriched diets: effects on plasma lipoproteins in normolipidemic subjects", AMERICAN JOURNAL OF CLINICAL NUTRITION, 50:786–793, 1989) Nonetheless, the use of soy protein as part of a combination of dietary cholesterol-lowering ingredients might contribute to a medically significant decrease in LDL cholesterol.

The cholesterol-lowering mechanism of soy protein is unclear. Part of the effect can be explained by the amino acid composition of proteins. (Huff et al., "Plasma cholesterol levels in rabbits fed low fat, cholesterol-free, semipurified diets: Effects of dietary proteins, protein hydrolysates and amino acid mixtures", ATHEROSCLEROSIS 28:187–195, 1977) Although the substitution of a supplement containing 5–10 g of plant protein for part of the animal protein in the diet would be unlikely by itself to cause a medically significant decrease in blood cholesterol levels, the use of soy protein as part of a combination of dietary cholesterol-lowering ingredients might contribute to a medically significant decrease in LDL cholesterol.

There is very little published scientific information on diets that combine known cholesterol lowering ingredients.

There is provided in accordance with the present invention a nutritional product having a solid matrix comprising protein, fat and carbohydrate, said matrix having disposed therein dietary fiber encapsulated in zein. The preferred dietary fiber is guar encapsulated with a coating of at least about 20% add-on zein. The protein is preferably a soy protein and may further include calcium caseinate, and/or oat protein. The fat is preferably selected from the group consisting of vegetable oils containing less than 25% saturated fatty acids, by weight. Examples of such vegetable oils are rice bran oil, canola oil, and corn oil.

FIRST ANIMAL STUDY

This study investigated, using a rat model, the cholesterol-lowering effect of four soluble polysaccharides which are highly fermentable in the cecum, but yield different fermentation products and differ in their capacity to bind bile acids. Male Wistar rats were randomly assigned to one of five diet groups: control, pectin, guar gum, gum arabic or β-cyclodextrin. The four test compounds were added to the control diet as a replacement of wheat starch.

Pectin is a highly branched galacturonic acid polymer which has effective gelforming properties, and a high capacity to bind bile acids and to interact with lipid digestion. (Koseki et al., "Effects of gum arabic and pectin on the emulsification, the lipase reaction, and the plasma cholesterol levels in rats", AGRICULTURAL BIOLOGICAL CHEMISTRY 53(12):3127–3132, 1989; Pfeffer et al., "Molecular interactions with dietary fiber components. Investigation of the possible association of pectin and bile acids", JOURNAL OF AGRICULTURAL FOOD CHEMISTRY, 29:455–461, 1981) Pectin is readily broken down by the large intestine microflora. Cholesterol lowering effects have consistently been reported with pectin. (Ahrens et al., "Effects of oral and intracecal pectin administration on blood lipids in mini pigs", JOURNAL OF NUTRITION; 116:70–76, 1986; Fernandez, et al, "Prickly pear (Opuntia sp) pectin reverses low density lipoprotein receptor suppression induced by a hypercholesterolemic diet in guinea pigs", JOURNAL OF NUTRITION, 122:2330–2340, 1992; Kay et al., "Effect of citrus pectin on blood lipids and fecal steroid excretion in man", AMERICAN JOURNAL OF CLINICAL NUTRITION, 108:630–639, 1978; Reddy et al., "Effect of dietary wheat bran, alpha, pectin and carrageenan on plasma cholesterol and fecal bile acid and natural sterol excretion in rats", JOURNAL OF NUTRITION, 110:1247–1254, 1980) This cholesterol lowering effect may be modulated by factors such as dietary lipid, especially cholesterol. (Kelley et al., "Effect of pectin, gum arabic and agar on cholesterol absorption, synthesis, and turnover in rats", JOURNAL OF NUTRITION, 108:630–639, 1978; Vigne et al., "Effect of pectin, wheat bran and cellulose on serum lipids and lipoproteins in rats fed on a low or high-fat diet", BRITISH JOURNAL OF NUTRITION, 58:405–413, 1987)

Gum arabic is also a galacturonic acid polymer with a high cation-binding capacity, but it lacks gelling properties. Despite its lack of gelling properties, gum arabic may lower cholesterol. Upon fermentation of gum arabic in the colon, $Ca^{2+}$ ions released may form insoluble complexes with bile acids, thus enhancing their excretion.

Guar gum is a neutral galactomannan that exhibits a low cation-binding capacity. It forms gels in the small intestine which may trap some organic materials such as bile acids. Guar gum is known to lower serum cholesterol in several animal species and in humans. (Chen et al., "Effects of guar gum and wheat bran on lipid metabolism of rats", JOURNAL OF NUTRITION, 109:1028–1034, 1979; Gallaher et al., "Viscosity and fermentability as attributes of dietary fiber responsible for the hypocholesterolemic effect in hamsters", JOURNAL OF NUTRITION, 123:244–252, 1993; Ide, et al. "Hypolipidemic effects of guar gum and its enzyme hydrolysate in rats fed highly saturated fat diets", ANNALS OF NUTRITION AND METABOLISM, 35:34–44, 1991; Jenkins et al. "Effects of pectin, guar gum and wheat fiber on serum cholesterol", THE LANCET, May 1975, pp 1116–1117)

Some oligosaccharides have been found to affect cholesterol metabolism to the same extent as the complex polysaccharides. β-cyclodextrin is a cyclic oligosaccharide that forms inclusion complexes with a variety of organic and inorganic molecules, in particular cholesterol and bile acids. (Riottot et al., "Hypolipidemic effects of β-cyclodextrin in the hamster and in the genetically hypercholesterolemic Rico rat", LIPIDS, 28:181–188, 1993) Cyclodextrins are fermentable (Flourie et al., "Fate of β-cyclodextrin in the human intestine", JOURNAL OF NUTRITION, 123:676–680, 1993) but the major end-product of their fermentation is propionate. (Levrat et al., "Role of propionic acid and bile acids excretion in the hypocholesterolemic effects of oligosaccharides in rats", JOURNAL OF NUTRITION, 124(4):531–538, 1994) By comparing these polysaccharides in rats adapted to high-lipid diets supplemented with 0.1% cholesterol, the respective effects of bile acid excretion and cecal fermentation on cholesterol transport and metabolism were evaluated.

METHOD

Male wistar rats (IFFA-CREDO, L'Arbresle, France) were fed a commercial pellet diet (A03 pellets, U.A.R., Villemoisson/Orge, France) until body weight reached approximately 150 g. Groups of 8 rats were fed semi-purified diets as a moistened powder for 21 days. The diets contained the following (g/100 g, dry weight): 18 g casein (Louis Francois, Paris, France), 57.4 g; wheat starch (L. Francois); 17.5 g peanut oil; 0.1 g cholesterol (Sigma, St. Louis, Mo.); 0.1 g vitamin mixture (U.A.R.); 6 g mineral mixture (U.A.R.). In the fiber-containing diets, 7.5 g of the wheat starch was replaced by 7.5 g pectin, guar gum or gum arabic (TIC gums, Belcamp, Md., U.S.A.) or β-cyclodextrin (Roquettes, Lestrem, France). The animals were housed two per cage. The cages had wire bottoms to limit coprophagy and maintained in temperature controlled rooms at 22° C. with the dark period from 10:00 p.m. to 8:00 a.m. The animals were maintained and handled according to the recommendations of the appropriate Institutional Ethics Committee.

Rats were sampled at the end of the dark period in the early morning, a time at which cecal fermentations are still very active. They were anesthetized with sodium pentobarbital (40 mg/kg) and maintained on a hot plate at 37° C. One ml of blood from each animal was placed in a plastic tube containing heparin and centrifuged at 10,000 × g for 15 minutes. After centrifugation, plasma was removed and kept at +4° C. for lipid and lipoprotein analysis. After blood sampling, the cecum and its contents were removed and weighed. Approximately 1 g of cecal content was transferred into microfuge tubes that were immediately frozen at −20° C. Plasma lipoproteins were separated by ultracentrifugation on a density gradient, as described by Serougne et al, 1987. The gradient was then fractionated (500 μL fractions) and kept at 4° C. for lipid analysis.

Bile acids were analyzed on cecal supernatants if soluble, or after extraction from untreated cecal samples or feces by 10 vol. ethanolic KOH using the reaction catalyzed by 3 α-hydroxysteroid dehydrogenase (EC 1.1.1.50; Sigma) as described by Turley et al., "Reevaluation of the 3 alpha-hydroxysteroid dehydrogenase assay for total bile acids in bile", JOURNAL OF LIPID RESEARCH, 19:924–928, 1978. Total cholesterol (BioMerieux, Charbonnieres-les-Bains, France) was determined in plasma and lipoprotein fractions by enzymatic procedures. A polyvalent control serum (Biotrol-33 plus) was treated in parallel to samples and served as control of accuracy of results in triglycerides and cholesterol analysis.

The cecal bile acid pool was calculated as cecal concentration (μmol/g) × cecal content volume (mL). Values are given as means ± SEM and, where appropriate, significance of differences between mean values was determined by analysis of variance (ANOVA) and multiple range comparisons by Fisher's PLSP procedures (Stat view 512 +,Brain Power, Calabasas, Calif., U.S.A.). Where necessary to achieve homogeneity of variance, the data were subjected to logarithmic transformation. Values of $P<0.05$ were considered significant.

RESULTS

The presence of soluble fibers or oligosaccharides in the diets did not affect the animals' food intake or the daily weight gain. Significant results of this experiment are presented below in Table 2 which shows that pectin, guar gum and β-cyclodextrin were highly effective in lowering plasma cholesterol concentrations (−22%, −27% and −37%, respectively), whereas rats fed the gum arabic diet exhibited only a moderate decrease in cholesterol levels (−13%). More importantly, LDL cholesterol levels, which increase the risk of atherosclerosis and coronary heart disease, were significantly lowered by guar gum (−45%) and β-cyclodextrin (−52%).

TABLE 2

EFFECT OF SOLUBLE FIBERS OR OLIGOSACCHARIDES ON PLASMA CHOLESTEROL AND LDL LEVELS[1]

| DIET | PLASMA CHOLESTEROL mg/mL | LDL CHOLESTEROL mg/mL |
|---|---|---|
| Control | 0.67 ± 0.03[a] | 0.27 ± 0.11[a] |
| Pectin | 0.52 ± 0.03[c] | 0.25 ± 0.04[a] |
| Gum arabic | 0.58 ± 0.02[b] | 0.23 ± 0.02[a] |
| Guar gum | 0.49 ± 0.03[c] | 0.15 ± 0.02[b] |
| β-Cyclodextrin | 0.42 ± 0.02[c] | 0.13 ± 0.02[b] |

[1]Each value is the mean ± SEM (n = 12) except in the group fed β-cyclodextrin (n = 10). Values within a column not sharing a superscript letter are significantly different (P < 0.05). The effect of dietary treatment was examined by ANOVA and multiple range comparison by Fisher's protected least significant procedures.

The present results are consistent with the view that the fibers that reduce the ileal reabsorption of bile acids and increase their excretion are the most hypocholesterolemic. Pectin and guar gum impair the ileal reabsorption of bile acids, thereby increasing the cecal pool and excretion of bile acids, probably by virtue of their high viscosity in the gut. β-cyclodextrin, in contrast, has a very potent effect on bile acid absorption which is attributable to its capacity to entrap or encapsulate sterols without substantial changes in luminal viscosity.

For fibers of similar viscosity, a higher fermentability seems associated with a more potent cholesterol-lowering effect. The breakdown of the fibers by the cecal microfora should release the bound bile acids in the lumen, allowing their absorption by the colonic epithelium. In fact, a variety of processes, including acidification of the colonic lumen, binding to calcium phosphate or to microorganisms (the concentration of which is enhanced by fermentation of dietary fiber) limits the concentration of soluble bile acids, thereby reducing their reabsorption. (Remesy et al., "Cecal Fermentations in Rats Fed Oligosaccharides (Inulin) are Modulated by Dietary Calcium Level", AMERICAN JOURNAL OF PHYSIOLOGY, 264:G855–G862, 1993) These observations support the hypothesis that fermentation prevents any significant colonic reabsorption of bile acids.

TABLE 3

EFFECTS OF SOLUBLE FIBERS OR OLIGOSACCHARIDES ON CECAL BILE ACID AND THEIR FECAL EXCRETION[1]

| | CECAL BILE ACIDS | | | FECAL EXCRETION | |
|---|---|---|---|---|---|
| | | | | FECES | BILE |
| DIET | TOTAL μmol/g | SOLUBLE % | POOL μmol/cecum | WEIGHT g/d | SALTS μmol/d |
| Control | 1.94 ± 0.13[ab] | 73 | 4.50 ± 0.26[a] | 3.42 ± 0.22[a] | 9.8 ± 0.8[a] |
| Pectin | 2.43 ± 0.15[b] | 25 | 8.03 ± 0.52[c] | 5.80 ± 0.41[c] | 15.1 ± 1.2[c] |
| Gum Arabic | 1.74 ± 0.20[a] | 31 | 5.80 ± 0.40[b] | 5.09 ± 0.38[bc] | 12.4 ± 1.3[b] |
| Guar Gum | 4.02 ± 0.46[c] | 21 | 14.2 ± 1.7[b] | 5.75 ± 0.34[c] | 19.4 ± 1.7[d] |
| β-Cyclodextrin | 7.74 ± 0.59[d] | 32 | 30.1 ± 9.6[c] | 4.80 ± 0.33[b] | 38.6 ± 3.5[e] |

[1]Each value is the mean ± SEM. n = 12, except in the group fed β-cyclodextrin (n = 10). Values within a column not sharing a superscript letter are significantly different (P < 0.05). The effect of dietary treatment was examined by ANOVA and multiple range comparison by Fisher's protected least significant procedures.

It was concluded that both guar gum and β-cyclodextrin increase bile acid excretion and decrease blood total cholesterol and LDL cholesterol levels in rats. Although both of these substances would probably be acceptable cholesterol lowering food ingredients, β-cyclodextrin has not yet been fed at therapeutic concentrations to a large number of people. Guar gum, in contrast, as indicated in Table 1 had been fed in 22 separate studies to a total of over 400 people. Therefore, guar gum was selected as one of the active ingredients to be evaluated in the manufacture of the food bar prototypes described below.

FOOD BAR EXAMPLE 1

Many attempts were made to manufacture an acceptable food bar matrix containing unencapsulated guar gum and free of partially or fully hydrogenated fat. For example the order of adding ingredients and mixing times was varied, but without satisfactory results. Food Bar Prototype Number 1 is typical of these attempts. As used herein and in the claims a nutritional product's or a food bar's "solid matrix" is a nutritional product or food bar without any external coating thereon.

TABLE 4

RECIPE FOR FOOD BAR PROTOTYPE NUMBER 1

| INGREDIENT | CONCENTRATION BY PERCENT WEIGHT OF BAR |
|---|---|
| High Fructose Corn Syrup | 25.71 |
| Oat Bran[1] | 21.17 |
| Guar[2] | 12.35 |
| Soy Protein | 11.44 |
| Rice Bran Oil | 10.13 |
| Polydextrose | 6.62 |
| Glycerin | 6.18 |
| Crisp Rice | 4.45 |
| Dicalcium Phosphate | 0.97 |
| Lecithin | 0.59 |
| Citric Acid | 0.39 |

[1]The "oat bran" used was actually a mixture comprising, by weight, 26.25% oat fiber, 62.128% oat flour and 11.622% soy protein.
[2]The guar was obtained from TIC Gums and was designated by their product code "8/22A", which is described below in the paragraph preceding "ENCAPSULATION EXPERIMENT 1".

Manufacturing Procedure:

Food Bar Prototype Number 1 was prepared in a Hobart mixer. All ingredients were placed in the mixer and mixed at room temperature (24°±10° C.). The first ingredients placed in the mixer were the soy protein, dicalcium phosphate, and citric acid and they were mixed until blended. The rice bran oil, and lecithin were then added to the other ingredients and mixed until blended. The guar was then added to the ingredient blend and mixed therewith until blended. The polydextrose, oat bran, and crisp rice, were then added and mixed until blended. The final ingredients added to the blend were the high fructose corn syrup, and glycerin which were mixed with the other ingredients until blended. The batch was then dumped on to the bench top and rolled out using a typical rolling pin to a uniform thickness. The batch was cut into bars with a spatula then cooled in a refrigerator to between 0° and 10° C. At no time were the food bars-or the blend of ingredients subjected to elevated temperatures for cooking or baking. Of course, friction due to mixing could elevate the temperature of the blend a few degrees. The bars were then packaged in a low density polyethylene/foil wrap.

The texture of this prototype food bar and all of the other prototype food bars described herein was determined using a Stevens L.F.R.A. Texture Analyzer. This instrument measures the amount of "grams of force"[that it takes to move a probe 3 mm into a bar at a speed of 0.2 mm/sec. The sample size is one bar, with five measurements taken per bar. The five measurements are averaged together and recorded as grams of force. The texture of food bar prototype number 1 was determined several times over a period of weeks and the results are presented in TABLE 5.

TABLE 5

TEXTURE TESTING FOR FOOD BAR PROTOTYPE NUMBER 1

| WEEK | FOOD BAR HARDNESS |
|---|---|
| 0 | 82 |
| 2 | 342 |
| 4 | 454 |
| 6 | 531 |
| 8 | 478 |

Inasmuch as a hardness of 400 or greater is unacceptably difficult to chew, this prototype and others containing unencapsulated guar and desirable levels of hydrogenated fat were not acceptable as a commercial product. Other problems which were observed were food bars becoming dried out, hardened, crumbling, or even turning into a powder.

FOOD BAR EXAMPLE 2

Food Bar Prototypes Number 2 and 3 were made with unencapsulated guar according to the teachings of U.S. Pat. No. 4,496,606. While this patent cites literature acknowledging use of dietary fiber, eg. guar, to treat hypercholestolemia the objective of their invention is a food bar for consumption as a diet supplement by Type II diabetics to improve glucose tolerance and reduce insulin requirements. Food Bar Prototype Number 2 was manufactured according to EXAMPLE 1 of U.S. Pat. No. 4,496,606, although as closely as possible, some ingredients were not fully described therein.

TABLE 6

RECIPE FOR FOOD BAR PROTOTYPE NUMBER 2

| INGREDIENT | CONCENTRATION BY PERCENT WEIGHT OF BAR |
|---|---|
| High Fructose Corn Syrup | 28.43 |
| Chocolate Confectionery Coating | 20.59 |
| Oat Cereal[1] | 15.69 |
| Wheat Germ | 12.75 |
| Guar[2] | 10.78 |
| Fructose | 5.88 |
| Partially Hydrogenated Soybean and Cottonseed Oils[3] | 5.39 |
| Sodium Chloride | 0.49 |

[1]Generic oat cereal ground up with a mortar and pestle.
[2]The guar was obtained from TIC Gums and was designated by their product code "8/22A", which is described below in the paragraph preceding "ENCAPSULATION EXPERIMENT 1".
[3]Crisco ®

Manufacturing Procedure:

The first step in manufacturing Food Bar Prototype Number 2 was to prepare the confectionery coating. This solid chocolate confectionery coating (solid at temperatures less than 32° C.) was melted by placing it in a beaker and heating it to 43°±10° C. The first ingredient placed in the Hobart mixer was the melted confectionery coating. All remaining ingredients were added to the mixer at room temperature (24°±10° C.). The high fructose corn syrup and partially hydrogenated soybean/cottonseed oils were added to the confectionery coating in the mixer and mixed until blended. The guar was then added and mixed until blended. The oat cereal, wheat germ, fructose and salt were then added and mixed until blended. The batch was then dumped onto a bench top and rolled out using a typical rolling pin to a uniform thickness. The batch was cut into bars with a spatula then cooled in a refrigerator to between 0° and 10° C. At no time were the food bars subjected to elevated temperatures for cooking or baking. Of course friction due to mixing could elevate the temperature of the blend a few degrees. The bars were then packaged in a low density polyethylene/foil wrap.

The texture of these prototype food bars was determined several times over a period of weeks using the method described above in Food Bar Example 1, and the results are presented in TABLE 7.

TABLE 7

TEXTURE TESTING FOR FOOD BAR PROTOTYPE NUMBER 2

| WEEK | FOOD BAR HARDNESS |
| --- | --- |
| 0 | 138 |
| 2 | 189 |
| 4 | 182 |
| 6 | 271 |
| 8 | 235 |
| 16 | 296 |
| 24 | 323 |

Food Bar Prototype Number 2 contained about 11% hydrogenated fat, by weight, in the food bar matrix which is an effective moisture barrier for the guar. Although the texture test results were acceptable, in a taste test of Food Bar Prototype Number 2, there was a considerable amount of tooth packing. However the taste was good, possibly due to the confectionery coating and high fat content of the food bar matrix. The inclusion of hydrogenated fat in such a food product provides saturated fat and an undesirably high caloric content.

FOOD BAR EXAMPLE 3

Food Bar Prototype Number 3 was manufactured according to EXAMPLE 2 of U.S. Pat. No. 4,496,606 as closely as possible, although some ingredients were not fully described therein.

TABLE 8

RECIPE FOR FOOD BAR PROTOTYPE NUMBER 3

| INGREDIENT | CONCENTRATION BY PERCENT WEIGHT OF BAR |
| --- | --- |
| High Fructose Corn Syrup | 28.99 |
| Corn Cereal[1] | 23.35 |
| Wheat Flour | 18.48 |
| Guar[2] | 8.75 |
| Chocolate Confectionery Coating | 8.75 |
| Fructose | 7.30 |
| Molasses | 3.89 |
| Sodium Chloride | 0.49 |

[1]Corn flakes ground up with mortar and pestle.
[2]The guar was obtained from TIC Gums and was designated by their product code "8/22A" which is described below in the paragraph preceding "ENCAPSULATION EXPERIMENT 1".

Manufacturing Procedure:

The first step in manufacturing Food Bar Prototype Number 3 was to prepare the confectionery coating. This solid chocolate confectionery coating (solid at temperatures less than 32° C.) was melted by placing it in a beaker and heating it to 43°±10° C. The first ingredient placed in the Hobart mixer was the melted confectionery coating. All remaining ingredients were added to the mixer at room temperature (24°±10° C.). The high fructose corn syrup and molasses were added to the confectionery coating in the mixer and mixed until blended. The guar was then added and mixed until blended. The corn cereal, wheat flour, fructose and salt were then added and mixed until blended. The batch was then dumped on to a bench top and rolled out using a typical rolling pin to a uniform thickness. The batch was cut into bars with a spatula then cooled in a refrigerator to between 0° and 10° C. At no time were the food bars subjected to elevated temperatures for cooking or baking. Of course, friction due to mixing could elevate the temperature of the blend a few degrees. The bars were then packaged in a low density polyethylene/foil wrap.

The texture of these prototype food bars was determined several times over a period of weeks using the method described above in Food Bar Example 1, and the results are presented in TABLE 9.

TABLE 9

TEXTURE TESTING FOR FOOD BAR PROTOTYPE NUMBER 3

| WEEK | FOOD BAR HARDNESS |
| --- | --- |
| 0 | 198 |
| 2 | 252 |
| 4 | 271 |
| 6 | 298 |
| 16 | 436 |
| 24 | 531 |

Texture test results for Food Bar Prototype Number 3 were not acceptable, and in a taste test there was a significant amount of tooth packing. Food Bar Prototype number 3 contained at least about 3% hydrogenated fat by weight. An attempt was made in this prototype to minimize hydrogenated fat, instead of confectionery peanut coating, for example by using a low fat confectionery coating. However, in Example 2 of U.S. Pat. No. 4,496,606 a 55 g bar contained 11 g of fat, most of which appears to be hydrogenated fat.

ENCAPSULATION OF DIETARY FIBER

A nutritional product in accordance with the present invention is a solid matrix comprising protein, fat and carbohydrate, said matrix having disposed therein particles comprising a dietary fiber encapsulated in zein. Preferably the encapsulated dietary fiber is guar encapsulated in a coating of at least about 20% add-on zein.

Prolamines form the main protein components of cereal grains and flour. Unlike all other proteins, they can be extracted from flour with 80 percent alcohol, but they are insoluble in absolute alcohol and water. The most important prolamines are zein, gliadin, and hordein. Zein is preferred in the present invention.

The zein component for the coating layer preferably comprises zein with an ash content of 2% or less by weight. The method used to determine ash is in the USP XXII, "Residue on Ignition", sulfated. The zein used in many of the examples set forth herein was F 4000, manufactured by Freeman Industries, Tuckahoe, N.Y., U.S.A., with an ash content of about 1.1% by weight. The plasticizer may be generally selected from the group consisting of food grade glycols including triethylene glycol and propylene glycol, acetylated glycerides, oleic acid, lactic acid acetamide, ethylene glycol monooleate, glycerin, glycerol monostearate, dibutyl tartrate, and tricresol phosphate. A suitable hydrophobic substance used for the zein coating material comprises vegetable and animal fats, either unhydrogenated, hydrogenated, or partially hydrogenated, fatty acids, and glycerine esters of fatty acids, with representative materials comprising palm oil, palm kernel oil, soybean oil, rapeseed oil, rice bran oil, sunflower oil, safflower oil, coconut oil, castor oil, MCT oil, also known as glycerine ester of C6–C18 fatty acids derived from coconut oil, and mixtures thereof. Other hydrophobic substances also useful herein may be selected from monoglycerides, distilled monoglycerides, acetylated monoglycerides, diglycerides, triglycerides, and mixtures thereof. The hydrophobic substance used in the examples set forth herein for various zein coats was MCT oil, glycerine ester of C6–C18 fatty acids derived from coconut oil, manufactured by Karlshamns, of Columbus, Ohio, U.S.A., under the trade name Captex® 355 or Durkex® 500, partially hydrogenated soybean oil, manufactured by Van Den Bergh Foods, Lisle, Ill., U.S.A..

The encapsulated guar gum may be prepared by a variety of coating techniques known in the art including fluid bed coating, coacervation, or a combination thereof, and the like, as disclosed in U.S. Pat. No. 4,384,004 to Cea et. al. Preferably, fluid bed coating with a Wurster column may be employed to apply the zein coating.

In the fluidized bed with Wurster column procedure as applied herein for applying the various coatings, the guar gum powder is suspended in an apparatus that creates a strong upward air current or stream in which the particles move. The stream passes through a zone of finely atomized coating material which causes the passing particles to be coated, after which the coated particles move upward through the Wurster column and then travel downward in a fluidized condition countercurrent to a flow of heated fluidized gas whereupon they are dried. The particles may reenter the upward stream for a further coating until the desired weight ratio of coating to active core has been obtained. The foregoing method and apparatus are known as the Wurster Process and are set forth in detail in the following U.S. Patents, the disclosures of which are incorporated herein by reference: U.S. Pat. Nos. 3,089,824; 3,117,027; 3,196,827; 3,241,520; and 3,253,944.

The prolamine coating materials are prepared for use as a solution capable of being uniformly atomized. The solubility of zein requires a solvent with both polar and non-polar groups in the proper ratio. The proper ratio of polar and non-polar groups can be obtained with single solvents or two or more solvent mixtures. Examples of suitable single solvents are acetic acid, lactic acid, propionic acid, and propylene glycol. The aqueous alcohols are preferred as solvents in many applications. Examples of suitable alcohol/water systems are methanol/water, ethanol/water, isopropanol/water, and n-butanol/water. To obtain complete solubility above the cloud point, the ratio of alcohol to water varies for each alcohol chosen and the mixed solvent final temperature. If desired, other ingredients such as plasticizers or hydrophobic substances may be added to improve the properties of the final coating. Suitable plasticizers include triethylene glycol, propylene glycol, oleic acid, lactic acid acetamide, ethylene glycol monooleate, glycerin, glycerol monostearate, dibutyl tartrate, and tricresol :phosphate. Suitable hydrophobic substances include vegetable and animal fats, either unhydrogenated, hydrogenated, or partially hydrogenated, fatty acids, and glycerine esters of fatty acids, with representative materials comprising palm oil, palm kernel oil, soybean oil, rapeseed oil, rice bran oil, sunflower oil, safflower oil, coconut oil, castor oil, MCT oil, also known as glycerine ester of C6–C18 fatty acids derived from coconut oil, and mixtures thereof. Other hydrophobic substances also useful herein may be selected from monoglycerides, distilled mono and diglycerides, acetylated mono and diglycerides, diglycerides, triglycerides, and mixtures thereof. The plasticizer may be added in known effective amounts within the scope of the invention. In general, amounts of about 5% to about 25% by weight of the zein are suitable.

The coating percentages used in the examples were calculated based on the amount of coating solution sprayed on the guar gum not actual zein analysis of the encapsulated product. Zein percentages are "added on" percentages defined as the weight of zein applied divided by the weight of guar gum charged to the fluid bed coater. As an example, for a charge of 500 g of guar gum a 20% zein add on coating would mean that a solution containing 100 g of zein was sprayed onto the guar. This coating percentage does not include any plasticizer which was usually added at a level of 20%, by weight, of the amount of zein.

Two sizes of guar gum particles were used in the following microencapsulation experiments. All of the guar gum particles were obtained from TIC Gums (Belcamp, Md. U.S.A.) Guar gum particles designated by TIC Gums as "8/22" (also referred to herein as "small" guar particles) are characterized by: a minimum viscosity of 3,000 cps (1% solution); and particle sizes in a sample such that a maximum of 4% of the particles pass through a USS sieve size #100 and a minimum of 75% of the particles pass through a USS sieve size #200; and a pH of 4 to 7. Guar gum particles designated by TIC Gums as "8/22A" (also referred to herein as "large" guar particles) are characterized by: a minimum viscosity of 3,000 cps (1% solution); and particle sizes in a sample such that a maximum of 25% of the particles pass through a USS sieve size #200 and 100% of the particles pass through a USS sieve size #60.

ENCAPSULATION EXPERIMENT 1

This experiment was conducted to evaluate the effect of particle size, as effected by the amount of coating material on a particle, on "mouth feel". "Mouth feel" is the sensory impression of food texture that a person perceives when eating food.

Guar gum was encapsulated in different levels of zein. The guar gum 8/22 (small guar particles) was obtained from TIC Gums (Belcamp, Md. U.S.A.). Because the particle size of the most of the guar was below 75 μm, a core of guar gum and zein was prepared before overcoating with zein. A solution of a coating material was prepared comprising zein (F4000, Freeman Industries, Tuckahoe, N.Y., U.S.A.) plus medium chain triglycerides (MCT oil) (Captex® 355, Karlshamms, Columbus, Ohio, U.S.A.) equaling 7.6% of the zein, as a 11.4% by weight solution of ethanol/water at a 90/10 weight/weight ratio. In a 4"/6" fluid bed unit with a see-through main chamber, the guar gum was initially granulated with a bottom spray nozzle and then coated using a bottom spray with a Wurster column insert. The coating solution was applied to 500 g of the guar gum at an initial rate of 8 g/minute. After 11 minutes the rate was increased to 9 g/minute, the atomizing air pressure for the spray nozzle was 15 psig. The fluidizing inlet air temperature varied between 43.9° and 46.7° C. with a corresponding air discharge temperature of about 25° to 32° C. After 5% zein by weight of the weight of the guar gum was applied, the guar gum was sieved to remove particles above 840 μm. The guar gum was then coated using the Wurster column insert with the same processing conditions. Samples were removed at zein levels of 20% and 40% by weight of the guar gum. At each sampling point the coated guar gum was sieved to remove particles greater than 840 μm before being returned to the unit for more coating. The encapsulation process was stopped after an amount of zein equal by weight to 60% of the weight of guar starting material was applied to the guar.

When incorporated into a food bar the particles coated with 20% add-on zein yielded a food product with good mouth feel. However, when particles coated with greater quantities of zein were incorporated in food bars the resultant products were adjudged to have unacceptable mouth feel which was described as "sandy" or "gritty".

ENCAPSULATION EXPERIMENT 2

The purpose of this experiment was to determine if the use of a different plasticizer with the zein would allow thinner coatings which would be as good of a moisture barrier as thicker coatings while giving the acceptable mouth feel of a thinner coating (smaller particles) when incorporated in a food product.

This example was very similar to encapsulation experiment where samples with different coating levels of zein were applied. The level of MCT oil was increased and the initial granulation process was changed. A solution of coating material was prepared comprising zein F4000 plus Captex® 355 equaling 20% of the zein, as a 12.5% by weight solution of ethanol/water at a 90/10 weight/weight ratio. In a 4"/6" fluid bed unit, the 8/22 guar gum (small guar particles) was initially granulated with a bottom spray nozzle and then coated using a bottom spray with a Wurster column insert. The coating solution was applied to 1000 g of the guar gum at a rate of 9 g/min. The atomizing air pressure for the spray nozzle was 15 psig. The fluidizing inlet air temperature varied between 44.4° and 50.9° C. with a corresponding air discharge temperature of about 21.1° to 27.2° C. After 10% zein by weight of the weight of the guar gum was applied, the guar gum was sieved to remove particles above 840 μm and below 125 μm. The guar gum was then coated using the Wurster column insert with the same processing conditions. Samples were removed at zein levels of 20% and 40% by weight of the guar gum. At each sampling point the coated guar gum was sieved to remove particles greater than 840 μm before being returned to the unit for more coating. The encapsulation process was stopped after 60% zein by weight of the guar was applied. This process resulted in less agglomeration than encapsulation experiment 1, but the powder flow within the chamber was slower which may have been due to the higher oil content in the coating solution.

When the particles coated with only 10% add on zein were incorporated in food bars, the bars become unacceptably hard in a short time, which indicated an insufficient moisture barrier on the guar. Although the MCT oil had good plasticising properties there is concern about undesirable effects on product flavor in other food products containing MCT oil.

ENCAPSULATION EXPERIMENT 3

This experiment was conducted to evaluate the coatability of larger size guar particles.

Guar gum was encapsulated in 20% add on zein using a 18" Wurster coater. The guar gum 8/22A used in this experiment has a slightly larger particle size, as described above. A solution of a coating material was prepared comprising zein F4000 plus Durkex® 500 equaling 20% of the zein, as a 15% by weight solution of ethanol/water at a 90/10 weight/weight ratio. The coating solution was applied to 35 kg of guar gum at an initial rate of 200 g/min and was gradually increased to 250 g/min over a 40 minute period. The atomizing air pressure for the spray nozzle was 80 psig. The fluidizing inlet air temperature varied between 44.4° and 46.7° C. with a corresponding air discharge temperature of between 26.1° to 38.9° C. After 20% zein by weight of the weight of the guar gum was applied, the process was stopped. The product was dried for 5 minutes and then removed from the column. 99% of the product was less than 40 mesh.

It was determined that larger size guar particles yielded better encapsulated particles of more uniform size than those obtained by coating the smaller size guar particles.

ENCAPSULATION EXPERIMENT 4

The objective of this experiment was to attempt to produce a final product of smaller encapsulated particles by using a series of sieving steps.

Guar gum was encapsulated in different levels of zein using a 18" Wurster coater. Guar gum 8/22 (small guar particles) was used in this experiment. A solution of a coating material was prepared comprising zein F4000 plus Durkex® 500 equaling 20% of the zein, as a 23.5% by weight solution of ethanol/water at a 90/10 weight/weight ratio. The coating solution was applied to 35 kg of the guar gum at a rate of 250 g/min. The atomizing air pressure for the spray nozzle was 80 psig. The fluidizing inlet air temperature varied between 43.9° and 46.7° C. with a corresponding air discharge temperature of between 24.4° to 40° C. After 10% zein by weight of the weight of the guar gum was applied, the process was stopped. The product was sieved to remove product greater than 420 μm and less than 150 μm. The sieved guar gum was returned to the Wurster column insert and coated with the same processing conditions. After a zein level of 20% add on was applied, the system was stopped. The product was dried for 5 minutes and then removed from the column. 97.5% of the product was less than 40 mesh.

While the yield of acceptable end product was high, this procedure would be cost prohibitive because of extra processing steps.

ENCAPSULATION EXPERIMENT 5

The objective of this experiment was to evaluate the use of rice bran oil as a hydrophobic material in the zein coating.

For this experiment the larger size guar gum (8/22A) was encapsulated in 25% add on zein with rice bran oil as the plasticizer. A solution of a coating material was prepared comprising zein F4000 plus rice bran oil equaling 20% of the zein by weight, as a 23.5% by weight solution of ethanol/water at a 90/10 weight/weight ratio. In a 4"/6" fluid bed unit, the guar gum was coated using a bottom spray with a Wurster column insert. The coating solution was applied to 500 g of the guar gum 8/22A at a rate of 9 g/min. The atomizing air pressure for the spray nozzle was 15 psig. The fluidizing inlet air temperature varied between 43.9° and 45° C. with a corresponding air discharge temperature of between 26.9° and 34.4° C. After 25% zein by weight of the weight of the guar gum was applied, the guar gum was sieved to remove particles above 420 μm and below 125 μm. 85.3% of the product was in the correct size range.

Rice bran oil did not appear to facilitate as good a coating process as the other plasticizers, but this could possibly be improved with changes in process and/or formulation.

ENCAPSULATION EXPERIMENT 6

The objective of this experiment was to evaluate the coating of larger guar particles with increased levels of zein.

For this experiment, the larger size guar gum particles (8/22A) were encapsulated in 30% add on zein with Durkex® 500 as the plasticizer. A solution of a coating material was prepared comprising zein F-4000 plus Durkex® 500 equaling 20% of the zein, as a 23.5% by weight solution of ethanol/water at a 90/10 weight/weight ratio. In a 4"/6" fluid bed unit, the guar gum was coated using a bottom spray with a Wurster column insert. The coating solution was applied to 500 g of the guar gum 8/22A at a rate of 9 g/min. The atomizing air pressure for the spray nozzle was 15 psig. The fluidizing inlet air temperature varied between 42.8° and 46.1° C. with a corresponding air discharge temperature of between 29.4° to 35.6° C. After 30% zein by weight of the weight of the guar gum was applied, the guar gum was sieved to remove particles above 420 μm and below 125 μm. 89.4% of the product was in the correct size range.

When the microencapsulated guar manufactured in this experiment was incorporated into food bars, the bars were crumbly and had an unacceptable "sandy" mouth feel.

ENCAPSULATION EXPERIMENT 7

The purpose of this experiment was to evaluate the use of carnauba wax as a coating material to reduce processing time with a dual coating process.

For this experiment, some of the product from experiment 3 was overcoated with carnauba wax. The carnauba (No. 120, Frank B. Ross Co. Inc., Jersey City, N.J., U.S.A.) was melted in a beaker and held at a temperature of 104.4° C. In a 4"/6" fluid bed unit, 500 g of the product from example 4 was coated using a bottom spray without a Wurster column insert. The molten wax was pumped at a temperature between 98.9° and 104.4° C. The atomizing air pressure was 15 psig. The fluidizing inlet air temperature varied between 51.6° and 53.3° C. with a corresponding outlet temperature of 39.4° to 41.7° C. After 75 g of the wax was applied the coating process was stopped.

When the microencapsulated particles manufactured in this experiment were incorporated into food bars, the resultant food bars became unacceptably hard within two months after manufacture.

ENCAPSULATION EXPERIMENT 8

The objective of this experiment was to evaluate zein particles coated only with carnauba wax.

For this experiment, the larger size guar gum particles (8/22A) were encapsulated in 44.8% add on carnauba wax. The carnauba wax (No. 120) was melted in a beaker and held at a temperature of 104.4° C. In a 4"/6" fluid bed unit, the guar gum was coated using a bottom spray without a Wurster column insert. The molten wax was applied to 500 g of the guar gum 8/22A. The atomizing air pressure for the spray nozzle was 15 psig. The fluidizing inlet air temperature varied between 53.9° and 72.2° C. with a corresponding air discharge temperature of between 33.1° and 36.7° C. After the carnauba wax was applied, the product was removed.

The microencapsulated guar manufactured in this experiment was not used in food bars because of the results of experiment 7.

ENCAPSULATION EXPERIMENT 9

The objective of this experiment was to evaluate the use of beeswax as a coating material.

For this experiment, the larger size guar gum was encapsulated in 23% add on beeswax. The beeswax (Frank B. Ross Co. Inc., Jersey City, N.J. U.S.A. was melted in a beaker and held at a temperature of 107.2° C. In a 4"/6" fluid bed unit, the guar gum was coated using a bottom spray without a Wurster column insert. The molten wax was applied to 500 g of guar gum 8/22A (large guar gum particles). The atomizing air pressure for the spray nozzle was 15 psig. The fluidizing inlet air temperature varied between 21.1° and 32.2° C. with a corresponding air discharge temperature of between 28.3° to 29.4° C. After the 5 minutes, the guar gum was starting to agglomerate so the inlet air temperature was reduced to 21° C. The process was stopped after 23% add on because of flow problems within the chamber.

When the encapsulated guar manufactured in this experiment was incorporated in food bars, the bars were unacceptably hard and crumbly and caused packing around the teeth of persons eating the bar.

ENCAPSULATION EXPERIMENT 10

The objective of this experiment was to evaluate the use of paraffin wax as a coating material.

For this experiment, the larger size guar gum particles (8/22A) were encapsulated in 40% add on paraffin wax. The wax (Paraffin 150/160, Frank B. Ross Co., Inc., Jersey City, N.J. U.S.A.) was melted in a beaker and held at a temperature of 104.4° C. In a 4"/6" fluid bed unit, the guar gum was coated using a bottom spray without a Wurster column insert. The molten wax was applied to 500 g of the guar gum 8/22A. The atomizing air pressure for the spray nozzle was 15 psig. The fluidizing inlet air temperature varied between 26.1° and 27.2° C. with a corresponding air discharge temperature of between 25.5° and 29.4° C. After 40% add on was applied the process was stopped.

When the encapsulated guar manufactured in this experiment was incorporated in food bars the bars hardened very quickly and caused packing around the teeth of persons eating the bar.

ENCAPSULATION EXPERIMENT 11

The purpose of this experiment was to evaluate the prospect of coating xanthan gum, which is a soluble high viscosity fiber.

For this experiment, xanthan gum was encapsulated in 20% add on zein with Durkex® 500 as the plasticizer. A solution of a coating material was prepared comprising zein F4000 plus Durkex® 500 equaling 20% of the zein, as a 23.5% by weight solution of ethanol/water at a 90/10 weight/weight ratio. In a 4"/6" fluid bed unit, the xanthan gum was coated using a bottom spray with a Wurster column insert. The coating solution was applied to 500 g of the xanthan gum at a rate of 9 g/min. The atomizing air pressure for the spray nozzle was 15 psig. The fluidizing inlet air temperature varied between 45° and 52.2° C. with a corresponding air discharge temperature of between 27.2° and 32.2° C. After 20% zein by weight of the weight of the xanthan gum was applied, the process was stopped.

To date the encapsulated xanthan gum has not been incorporated into a food product, but the coating process appears to have yielded a satisfactory product.

ENCAPSULATION EXPERIMENT 12

This experiment was conducted to evaluate the feasibility of larger scale (bigger batch size) coating of guar with zein using larger capacity coating equipment and a different plasticizer.

Guar gum was encapsulated in different levels of zein using a 18" Wurster coater. The small guar gum particles (8/22) were used in this experiment. A solution of a coating material was prepared comprising zein F4000 plus partially hydrogenated vegetable oil (Durkex® 500, Van den Bergh Foods Co., Lasle, Ill. U.S.A.) equaling 20% of the zein, as a 23.5% by weight solution of ethanol/water at a 90/10 weight/weight ratio. The coating solution was applied to 50 kg of the guar gum at an initial rate of 175 g/min and was gradually increased to 215 g/min over a 30 minute period. Periodically the liquid line was flushed with 90/10 ethanol/water, if the liquid line pressure increased. The atomizing air pressure for the spray nozzle was 80 psig. The fluidizing inlet air temperature varied between 45.6° and 46.7° C. with a corresponding air discharge temperature of between 25° and 33.3° C. After 10% zein by weight of the weight of the guar gum was applied, the process was stopped to remove a sample. The guar gum (35 kg) was returned to the Wurster column insert and coated with the same processing conditions. After a zein level of 15% add on was applied, the system was stopped again, and a sample was removed. The encapsulation process was stopped after 20% zein by weight of the guar was applied. The product was dried for 5 minutes and then removed from the column. The product was sieved to remove product over 40 mesh (420 μm). 84% of the product was less than 40 mesh.

It was determined that a scale-up of the coating process if feasible and that the hydrogenated vegetable oil is a good plasticizer that did not haver any substantial effect on product taste. The microencapsulated guar produced in this experiment was employed in the "Second Animal Study" which is described below.

ENCAPSULATION EXPERIMENT 13

The objective of this experiment was to further refine the coating process.

Guar gum was encapsulated in 25% add on zein using a 18" Wurster coater. A solution of a coating material was prepared comprising zein F4000 plus Durkex® 500 equaling 20% of the zein, as a 23.5% by weight solution of ethanol/water at a 90/10 weight/weight ratio. The coating solution was applied to 35 kg of large guar gum particles (8/22A) at a rate of 240 g/min. The atomizing air pressure for the spray nozzle was 80 psig. The fluidizing inlet air temperature varied between 45° and 47.2° C with a corresponding air discharge temperature of between 28.9° to 37.8° C. After 25% zein by weight of the weight of the weight of the guar gum was applied, the process was stopped. The product was dried for 5 minutes and then removed from the column. The product was sieved to remove product over 40 mesh and underneath 140 mesh. 89.8% of the product was in the right range.

The microencapsulated guar manufactured with this procedure was employed in food bar prototype number 4 which was used in the "HUMAN CLINICAL STUDY OF FOOD BAR" which is described below.

ENCAPSULATION EXPERIMENT 14

The objective of this experiment was to improve the coating process and produce better microencapsulated guar for use in a solid food product.

Large guar gum particles (8/22A) were encapsulated in 25% add on zein using a 18" Wurster coater. A solution of a coating material was prepared comprising zein F4000 plus Durkex® 500 equaling 20% of the zein, as a 15% by weight solution of ethanol/water at a 90/10 weight/weight ratio. The coating solution was applied to 35 kg of the guar gum particles at a rate of 240 g/min. The atomizing air pressure for the spray nozzle was 80 psig. The fluidizing inlet air temperature varied between 38.9° and 47.2° C. with a corresponding air discharge temperature of between 24.4° and 35.6° C. After 25% zein by weight of the weight of the guar gum was applied, the process was stopped. The product was dried for 5 minutes and then removed from the column. The product was sieved to remove product over 40 mesh. 97.2% of the product was less than 40 mesh.

The encapsulated guar manufactured in this experiment has been incorporated in food bar prototypes 5,6,7 and 8 which are described below.

Encapsulation (i.e. microencapsulation) of guar with zein protein represents a significant modification of the physical properties of guar, which may modify the physiological effects of the guar. In order to verify that zein-encapsulated guar retained the cholesterol-lowering effective of native unencapsulated guar, a second animal study and a study in humans were conducted.

SECOND ANIMAL STUDY

The present study was designed to determine, in an animal model with good predictive value for humans, what changes in serum cholesterol to expect in response to a diet in which rice bran oil, soy protein and zein microencapsulated guar gum are added at a level that approximates on a weight per calorie basis the dose that would be fed to human subjects to obtain a cholesterol-lowering effect. Rice bran oil and soy protein were added to the diets in these experiments because rice bran oil and soy protein, like guar gum, have been found to lower cholesterol in previous experiments.

Rice bran oil contains unusually high levels of unsaponifiable components (i.e. non-fatty acid containing components). Previous investigations with hamsters have shown that rice bran oil reduces plasma cholesterol and prevents fatty streak formation, the earliest event in atherosclerosis. (Nicolosi et al, "Comparative effects of rice bran oil, soybean oil and coconut oil on lipoprotein levels, low density lipoprotein oxidixability and fatty streak formation in hypercholesterolemic hamsters." ARTERIOSCLEROSIS, 11:1603a, 1991) In cynomolgus monkeys, when rice bran oil was substituted at varying levels for the dietary fat of a standard American diet, there was a 1% reduction in low density lipoprotein cholesterol for every 1% of calories as rice bran oil added to the diet, (Nicolosi et al., "Rice bran oil lowers serum total and low density lipoprotein cholesterol and apoB levels in nonhuman primates", ARTERIOSCLEROLEROSIS, 88(2–3):133–142, 1991) When 20% of calories as rice bran oil was added to human diets, there was a 19.7% decrease in LDL cholesterol after 5 weeks on the diet. (Lichenstein et al, "Rice bran oil consumption and plasma lipid levels in moderately hypercholesterolemic humans", ARTERIOSCLER-THROMBOSIS, 14(4):549–56; 1991) The triglycerides of rice bran oil contain up to 20% saturated fatty acids and approximately equal amounts of polyunsaturated (40%) and monosaturated fatty acids (40%). Because rice bran oil is not particularly low in saturates, its cholesterol lowering action has been attributed to its poorly characterized unsaponifiable components.

STUDY DESIGN

In female cynomolgus monkey, an animal model that is highly predictive of changes in cholesterol levels in response to diet in humans, five diets were compared in a randomized crossover design. The first diet (A) was an average American diet which contained 36% of calories as fat, with saturated fat as approximately 15% of the calories. The next 4 diets (B, C, D, and E) were all American Heart Association Step 1 diets containing 30% of calories as fat, in which saturates made up slightly less than 10% of the calories. However, these 4 diets were modified by the addition of microencapsulated guar gum (to achieve 3.5% by weight guar gum), and soy protein (9% by weight). In addition, diets C, D, and E contained respectively 5, 10, and 20% of calories as physically refined rice bran oil. Physical refining is a method of edible oil processing that allows for the retention of non-saponifiable components. A sixth diet, an unmodified American Heart Association Step 1 diet (F) was fed at the end of the study after all the other diets had been completed. The diets were color-coded. Out of 20 monkeys, 19 finished all 5 periods of the study. Diet F was not part of the original protocol. After the animals completed diets A–E, all 19 monkeys were fed diet F for a period of 6 weeks. The composition of diets A–F are presented in Table 10.

EXPERIMENTAL DIETS

A. Average American Diet (AAD) (red)

B. Modified Step 1 diet. A cholesterol lowering fiber and soy protein were added. (blue/no color)

C. Modified Step 1 diet with 5% of calories as physically refined rice bran oil (yellow)

D. Modified Step 1 diet with 10% of calories as PR-RBO (green)

E. Modified Step 1 diet with 20% of calories as PR-RBO (orange)

F. Standard Step 1 diet (no color)

TABLE 10

| DIET COMPOSITIONS IN GRAMS PER 100 G DRY WEIGHT | | | | | | |
|---|---|---|---|---|---|---|
| | Diet A | Diet B | Diet C | Diet D | Diet E | Diet F |
| Casein | 7.96 | 5.7 | 5.7 | 5.7 | 5.7 | 15.5 |
| Soy Protein | 7.96 | 9.0 | 9.0 | 9.0 | 9.0 | 0 |
| Protein from ZMG* | 0 | 0.8 | 0.8 | 0.8 | 0.8 | 0 |
| Cystine | 0.19 | 0.18 | 0.18 | 0.18 | 0.18 | 0.18 |
| Dextrin | 31.42 | 34.0 | 34.0 | 34.0 | 34.0 | 34.0 |
| Sucrose | 22.61 | 24.5 | 24.5 | 24.5 | 24.5 | 24.5 |
| Coconut Oil | 5.53 | 3.53 | 2.95 | 2.36 | 1.18 | 3.53 |
| Olive Oil | 8.94 | 3.42 | 2.85 | 2.28 | 1.14 | 3.42 |
| Corn Oil | 3.07 | 7.18 | 5.98 | 4.78 | 2.39 | 7.18 |
| Rice Bran Oil | 0 | 0 | 2.35 | 4.71 | 9.43 | 0 |
| Cholesterol | 0.0782 | 0.0377 | 0.0377 | 0.0377 | 0.0377 | 0.0377 |
| Vitamin Mix | 0.57 | 0.55 | 0.55 | 0.55 | 0.55 | 0.55 |
| Choline | 0.34 | 0.33 | 0.33 | 0.33 | 0.33 | 0.33 |
| Salt Mix | 5.55 | 5.36 | 5.36 | 5.36 | 5.36 | 5.36 |
| Cellulose | 5.27 | 1.6 | 1.6 | 1.6 | 1.6 | 5.1 |
| Fiber from ZMG* | 0 | 3.5 | 3.5 | 3.5 | 3.5 | 0 |
| Banana Flavoring | 0.52 | 0.5 | 0.5 | 0.5 | 0.5 | 0.5 |
| Total (Dry Wt) | 100.00 | 100.19 | 100.19 | 100.19 | 100.14 | 100.2 |
| Water | 20.00 | 20.00 | 20.00 | 20.00 | 20.00 | 20.00 |
| Total (Wet) | 120.00 | 120.5 | 120.5 | 120.5 | 120.5 | 120.5 |
| Kcal/g (Wet) | 3.65 | 3.58 | 3.58 | 3.58 | 3.58 | 3.58 |
| Grams/Day (Wet) | 200 | 200 | 200 | 200 | 200 | 200 |
| Kcal/Day | 731 | 716 | 716 | 716 | 716 | 716 |
| Cholesterol | | | | | | |
| (mg/kcal) | 0.19 | 0.09 | 0.09 | 0.09 | 0.09 | 0.09 |
| (mg/day) | 139 | 65 | 65 | 65 | 65 | 65 |
| % KCAL: | | | | | | |
| FAT | 36.0 | 30.4 | 30.4 | 30.4 | 30.4 | 30.4 |
| CHO | 49.3 | 55.0 | 55.0 | 55.0 | 55.0 | 55.0 |
| PRO | 14.7 | 14.6 | 14.6 | 14.6 | 14.6 | 14.6 |
| Insoluble Dietary Fiber | 5.27 | 1.8 | 1.8 | 1.8 | 1.8 | 5.1 |
| Soluble Dietary Fiber | 0 | 3.5 | 3.5 | 3.5 | 3.5 | 0 |

*Zein microencapsulated guar

The dry diets were hydrated by adding 20% (w/w) water and poured into square plastic containers (100 g of wet diet per container) which were sealed and stored at −20° C. The monkeys were fed 2 squares of the diet per day, each 100 g supplying 358 kcal for a total of 716 kcal per day. To avoid errors, each diet was dyed and a colored card was placed on the cage.

Fasting blood samples were obtained after 4, 5, and 6 weeks on each diet. Blood was analyzed for lipids, including total cholesterol and HDL cholesterol. Blood was drawn from the iliac vein of monkeys into EDTA-containing tubes and plasma was harvested by low speed centrifugation. Plasma total cholesterol (TC) and triglycerides (TG) were quantified using enzymatic methods described in Allain et al., "Enzymatic determination of total serum cholesterol", CLINICAL CHEMISTRY, 20(4):470–481, 1974; Bucolo, "Quantitative determination of serum triglyceride by the use of enzymes", CLINICAL CHEMISTRY, 19(5):476–482, 1973) HDL-C was measured after phosphotungstate magnesium chloride precipitation of VLDL and LDL. The LDL-C fraction was determined by the difference between TC and HDL-C (the LDL-C fraction as measured included less than 15% VLDL-C when these diets were fed). All analyses were done by autoanalyser.

RESULTS

The monkeys adapted well to the diets. Nineteen animals completed all 5 diet periods (A–E) in the proper order, with total cholesterol and HDL cholesterol analyzed at weeks 4,5, and 6 in all 19 monkeys. Diet F was fed after diets A–E. Total and HDL cholesterol were measured at weeks 4 and 6 in all 19 monkeys.

After 6 weeks on the average American diet (diet A), the mean total cholesterol level in the 19 monkeys that completed the study was 242.6 mg/dl. When the animals were fed the diets supplemented with zein microencapsulated guar and soy protein, mean serum cholesterol levels ranged from 132.5 mg/dl to 144.1 mg/dl. These represent mean decreases ranging from 98.5 to 110 mg/dl, approximately 40% to 45% lower than with the standard American diet (diet A) ($p<0.001$). Cholesterol levels were not influenced by the amount of rice bran oil in the diets. Results are summarized in Table 11.

Decreases in total plasma cholesterol were entirely accounted for by decreases in LDL cholesterol. LDL cholesterol decreased from an average of 171.3 mg/dl after 6 weeks on the standard American diet (diet A) to between 62.8 mg/dl to 72.4 mg/dl after 6 weeks on the zein microencapsulated guar diets. This represents decreases of 58–63%. HDL cholesterol did not change.

The absence of effect of "physically refined" rice bran oil, even at levels as high as 20% of calories, was an unexpected result. In previous studies, when rice bran oil was added to the diet at 20% of calories in monkeys and in humans, serum cholesterol levels decreased by 20% relative to the standard American diet. In the present study, the large cholesterol lowering effect of zein microencapsulated guar and/or soy protein masked the cholesterol lowering effect of "physically refined" rice bran oil. It is possible that the presence of fat at the level of approximately 30% of calories is very important in potentiating the cholesterol-lowering effect of zein microencapsulated guar and/or soy protein, but clearly there was no difference between "physically refined" rice bran oil and a mixture of corn oil, olive oil and coconut oil under the present feeding conditions in this animal model.

components such as zein microencapsulated guar and soy protein.

Lipid levels in animals fed an unmodified Step 1 diet (Diet F)

As indicated in the methods section, these results were analyzed separately from diets A–E. When the same 19 monkeys that completed diets A–E were fed the unmodified Step 1 diet for 6 weeks (i.e. Step 1 diet without zein microencapsulated guar, soy protein or rice bran oil added), their cholesterol levels were 23.8% lower than they were on the average American diet (Diet A) and mean LDL cholesterol levels were 32.2% lower than they were on the average American diet (Table 11). That means that the unmodified Step 1 diet (Diet F) was only about 50–60% as effective as the modified step 1 diets (Diets B,C,D and E) at lowering cholesterol and LDL cholesterol: while the unmodified Step 1 diet (Diet F) reduced mean cholesterol levels from 243 to 185 mg/dl, the modified Step 1 diet (Diets B, C, D and E) reduced cholesterol another 40+ mg/dl to the range of 132–144 mg/dl.

Lipid changes over time

Plasma lipid levels varied as a function of time on each of the diets except Diet D (Table 12). When the average American diet was fed, cholesterol levels continued to increase over the 6 week period of the study (cholesterol levels were significantly higher at 6 weeks than at 4 weeks). In contrast, cholesterol levels decreased during feeding of Diets B, C, D and E which contained zein, microencapsulated guar and soy protein (cholesterol levels were lower at 6 weeks than at 4 weeks on diets C and E, and lower at 6 weeks than at 5 weeks on Diet B). Therefore, as the study progressed, the differences between Diets B, C, D and E which contained zein microencapsulated guar and soy protein, and the average American diet (Diet A) became more accentuated.

Although changes in LDL over time were not statistically significant (except on Diet E for which mean cholesterol was lower at week 6 than at week 4), there were clear trends that paralleled the changes observed for total cholesterol: the trend is upward for Diet A (average American diet) and downward in 3 of the 4 diets containing microencapsulated guar (date not shown). In contrast, there were no trends whatsoever in HDL over time. Therefore, it is reasonable to conclude that changes in total cholesterol over time resulted entirely from changes in the LDL fraction.

TABLE 11

| | MEAN PLASMA AND LIPOPROTEIN TOTAL CHOLESTEROL LEVELS AT 6 WEEKS[1] | | | | | |
|---|---|---|---|---|---|---|
| DIETS[3] | A Average American Diet | B Modified Step 1 | C Modified Step 1 with 5% RBO | D Modified Step 1 with 10% RBO | E Modified Step 1 with 20% RBO | F Standard Step 1 Diet |
| Total Cholesterol[2] | 242.6 ± 16.4 | 140.8 ± 6.1 | 139.6 ± 9.1 | 144.1 ± 8.3 | 132.5 ± 7.1 | 184.8 ± 10.3 |
| LDL Cholesterol[2] | 171.3 ± 19.0 | 70.0 ± 6.5 | 69.4 ± 9.8 | 72.4 ± 9.6 | 62.8 ± 6.7 | 116.1 ± 12.7 |
| HDL Cholesterol | 71.3 ± 5.9 | 70.8 ± 4.4 | 70.2 ± 3.7 | 71.7 ± 4.2 | 69.7 ± 3.6 | 68.7 ± 5.7[4] |

[1]Results are the mean ± SEM for 19 animals in mg/100 mL
[2]A > B–E ($P < 0.001$) and B–E < F ($P < 0.05$)
[3]Diet compositions are presented in Table 10
[4]F > D ($P < 0.05$)

It is likely that other types of rice bran oil may be equally as effective as "physically refined" rice bran oil when added to the diet in conjunction with other cholesterol lowering

TABLE 12

MEAN PLASMA TOTAL CHOLESTEROL LEVELS AFTER 4, 5 AND 6 WEEKS[1]

| DIETS[6] | A | B | C | D | E | F |
|---|---|---|---|---|---|---|
| 4 WEEKS | 229.5 ± 18.4 | 150.0 ± 6.5 | 156.0 ± 15.9 | 145.6 ± 8.1 | 153 ± 11.9 | 202.2 ± 17.5 |
| 5 WEEKS | 230.6 ± 15.9 | 152.1 ± 6.7 | 146.7 ± 13.0 | 138.1 ± 6.3 | 141.4 ± 9.0 | N/A |
| 6 WEEKS | 242.6 ± 16.4[2] | 140.8 ± 6.1[3] | 139.6 ± 9.1[4] | 144.1 ± 8.3 | 132.5 ± 7.1[5] | 184.8 ± 10.3 |

[1]Results are the means ± SEM for 19 animals in mg/100 mL
[2]Week 6 > Week 4, p = 0.03
[3]Week 6 < Week 5, p = 0.04
[4]Week 6 < Week 4, p = 0.02
[5]Week 6 < Week 4, p = 0.03
[6]Diet compositions are presented in Table 10
N/A = Date not available

HUMAN STUDY

The present study was initiated to determine whether rice bran oil, soy protein and zein-microencapsulated guar, the combination of ingredients that were effective in lowering cholesterol in monkeys, as described above, in the second animal study, could lower cholesterol in humans when incorporated into a nutritional product in accordance with the present invention. In this study said nutritional product according to the invention is a food bar referred to herein as the "active bar". The active bar was compared to a "control bar" containing ingredients known to have no cholesterol-lowering activity.

Clinical products. The compositions of the active and control bars are presented in Tables 13 through 16. Each 203 kcal 57.6 gram (g) active bar delivered on average 11.9 g of Association of Official Analytical Chemists (AOAC) measurable dietary fiber, including 9.2 g of dietary fiber from guar gum, 5.60 g of physically refined rice bran oil, and 5.60 grams of soy protein. The guar gum was microencapsulated with zein protein, which brought the total protein content of the active bar to 8.9 g. Each 215 kcal, 62 g control bar contained the following control ingredients: approximately 12.4 g of pea hull and Snowite oat fiber (both fiber sources contain 80–90% insoluble cellulosic fiber), 6.1 g of peanut oil, and a total of 9.3 g of protein from calcium caseinate and complete milk protein. Active and control bars were closely matched with regard to the calorie-providing macronutrients (carbohydrate, fat and protein), total calories, and total mineral content of which ash is an indication (including calcium).

TABLE 13

RECIPE FOR FOOD BAR PROTOTYPE NUMBER 4
"active bar"

| INGREDIENT | CONCENTRATION BY % WEIGHT of BAR | GRAMS/BAR |
|---|---|---|
| High Fructose Corn Syrup | 30.28 | 17.44 |
| Oat Bran[1] | 8.52 | 4.91 |
| Zein Encapsulated Guar[2] | 24.45 | 14.08 |
| Soy Protein | 9.72 | 5.60 |
| Rice Bran Oil[3] | 9.72 | 5.60 |
| Glycerin | 6.13 | 3.53 |
| Polydextrose | 4.76 | 2.74 |
| Crisp Rice | 4.42 | 2.55 |
| Dicalcium Phosphate | 0.96 | 0.55 |
| Lecithin | 0.58 | 0.33 |
| Citric Acid | 0.39 | 0.22 |

TABLE 13-continued

RECIPE FOR FOOD BAR PROTOTYPE NUMBER 4
"active bar"

| INGREDIENT | CONCENTRATION BY % WEIGHT of BAR | GRAMS/BAR |
|---|---|---|
| Flavor (Raspberry) | 0.07 | 0.04 |

[1]The "oat bran" used was actually a mixture comprising, by weight, 26.25% oat fiber, 62.128% oat flour and 11.622% soy protein.
[2]The guar gum was encapsulated as described above in ENCAPSULATION EXPERIMENT 13.
[3]Physically refined rice bran oil from Tsuno Rice Fine Chemical Co., Wakayama, Japan.

TABLE 14

NUTRITION PROVIDED BY "ACTIVE BAR"

34.7 g of carbohydrates (includes dietary fiber)
11.9 g of total dietary fiber (9.2 g of guar fiber)
6.5 g of fat:

| | |
|---|---|
| Saturated fatty acids | 20.4% |
| Monounsaturated fatty acids | 44.5% |
| Polyunsaturated fatty acids | 35.1% |

8.9 g of protein
1.0 g of ash (191 mg of calcium)
6.1 g water
203 Kcal

Manufacturing Procedure:

Food Bar Prototype Number 4 has been manufactured in commercial batch sizes ranging up to 390 kg. The type of mixer used was a double arm mixer. All ingredients added to the mixer were added and mixed at room temperature (24°±10° C.). The first ingredients placed in the mixer were the soy protein, dicalcium phosphate, and citric acid and mixed until blended. The rice bran oil, lecithin, and flavor were then added and mixed until blended. The zein microencapsulated guar was then added and mixed until blended. The polydextrose, oat bran, crisp rice, were added and mixed until blended. The final ingredients placed in the mixer were the high fructose corn syrup and glycerin and the product mixed until blended. The batch was then dumped into a double roll extruder and extruded at room temperature (24°±10° C.) and cut into a specified size by a cutting bar. Of course friction due to mixing could elevate the temperature of the blend several degrees. The bars are then cooled by a cooling tunnel to between 0° and 15° C. At no time were the food bars subjected to elevated temperatures for baking. Of course friction due to mixing or extruding could elevate the temperature of the blend a few degrees. The bars were then packaged in a low density polyethylene/foil wrap.

The texture of this prototype food bar was determined only at the time of manufacture using the method described above in Food Bar Example 1. At the time of manufacture the food bar hardness was 97. The texture of these particular foods bars at later times was not determined.

TABLE 15

RECIPE FOR "CONTROL" FOOD BARS

| INGREDIENT | Concentration by Percent Weight Of Bar | GRAMS/BAR |
|---|---|---|
| High Fructose Corn Syrup | 35.71 | 22.14 |
| Pea Outer Hull Fiber | 13.45 | 8.34 |
| Calcium Caseinate | 13.30 | 8.25 |
| Lodex | 10.12 | 6.28 |
| Peanut Oil | 9.85 | 6.11 |
| Snowite Oat Fiber | 6.95 | 4.06 |
| Crisp Rice | 4.15 | 2.57 |
| Complete Milk Protein | 3.65 | 2.26 |
| Glycerin | 2.07 | 1.28 |
| Soy Lecithin | 0.60 | 0.37 |
| Citric Acid | 0.49 | 0.30 |
| Raspberry Flavor | 0.06 | 0.04 |

TABLE 16

NUTRITION PROVIDED BY "CONTROL BAR"

38.3 g of carbohydrates (includes dietary fiber)
8.59 (analytical vs. 11.15 g of total dietary fiber expected)
6.6 g of fat:

| | |
|---|---|
| Saturated fatty acids | 20.4% |
| Monounsaturated fatty acids | 48.1% |
| Polyunsaturated fatty acids | 31.5% |

9.3 g of protein
0.97 g of ash (192 mg of calcium)
6.8 g water
215 Kcal

Subject Selection. Subjects were humans selected based on interest in the study and willingness to perform the actions required. They had to be in generally good health, particularly with regard to gastrointestinal function.

Design. The study was a randomized crossover study of 43 free-living subjects (18 females and 25 males) with a mean age of 35 years (range 23–59) in which the active bar was compared to a control bar. Of the 43 normal subjects who finished the study, 22 ate 1 (one) active bar per day for 7 days and 2 (two) active bars for 14–16 days (Period I=21–23 days total). Period I was followed by a 12–14 day washout period, followed by the consumption of 1 (one) control bar per day for 7 days and 2 (two) control bars per day for 14–16 days (Period II=21–23 days total). As used herein the period during which a subject consumed the active bar is referred to as the "active bar period" and the period during which a subject consumed the control bar is referred to as the "control bar period". The other 21 subjects followed the same schedule in reverse order, starting with control bars during Period I, followed by the washout period, followed by the consumption of active bars during Period II. In order to balance the number of days on each bar, the subjects whose bloods were initially drawn on Monday during the first period were switched to a Wednesday draw for a second period and vice versa.

Methods. After a thorough overnight fast, blood was drawn between 7:30 and 9AM prior to the study (baseline) and at the end of the control bar and active bar periods and blood plasma analyzed by a standard blood chemistry method by Roche Laboratories, Dublin, Ohio, U.S.A.

In order to assess whether the consumption of 2 bars per day was changing the typical diet of these subjects, 3-day diet records were requested during the following time periods:

1. A Thursday, Friday and Saturday just prior to the beginning of the study (Baseline).
2. A Thursday, Friday and Saturday prior to the end of study Period I.
3. A Thursday, Friday and Saturday prior to the end of Period II.

The diet records were recorded in record books that contained detailed instructions on portion sizes and description of the foods that were recorded. The record books were returned to a dietitian who was able to contact the subjects directly if food items of amount, were unclear and translate the data into daily intakes using a standard computer program (Nutritionist IV, San Bruno, Calif.).

Statistical analysis. For continuous/normally distributed variables, the statistical analysis was done by two-period cross-over ANOVA. The effects of sequence (diet x period interaction), period (diet x sequence interaction) and the direct effect of diet were included in the analysis. Whenever there was a sequence effect ($p<0.10$), the treatments were compared using data from the first period only. All other results were considered significant if $p<0.05$.

RESULTS

Blood Lipids. Mean serum, LDL, and HDL cholesterol levels were not significantly different at baseline and following the control period, indicating that the control bar was neutral with regard to serum lipids (Table 17). During the active bar period, mean serum cholesterol and LDL cholesterol levels decreased by 25 mg/dL and 23 mg/dL, respectively, compared to the control bar period (serum cholesterol decreased by 13.2% and LDL cholesterol decreased by 18.6%). HDL cholesterol levels also decreased significantly during the active bar period, relative to the control bar period but not relative to the baseline measurements. As a proportion of total cholesterol decrease, decreases in LDL cholesterol consistently accounted for over 90% of the total cholesterol decrease.

TABLE 17

SERUM, LDL and HDL CHOLESTEROL LEVELS
(means ± SEM, mg/dL

| | Total cholesterol | LDL cholesterol | HDL cholesterol |
|---|---|---|---|
| Baseline | 193 ± 5 | 127 ± 5 | 43 ± 2 |
| Control | 191 ± 4 | 125 ± 4 | 45 ± 2 |
| Active | 166 ± 4* | 101 ± 3* | 42 ± 2** |

*p = <0.001, compared to control
**p = 0.002, compared to control

Serum Potassium and Bilirubin Levels. Serum potassium levels were significantly lower in the active bar group (Means±SEM: 4.11±0.05 on the active bar compared to 4.32±0.08 on the control bar) (p=0.01). Average potassium intake decreased from approximately 3000 mg/day at baseline to 2500 rag/day on either bar (control or active), indicating that the addition of either bar to the diet may displace some high potassium foods from the diet. This argues for supplementation of the bars with potassium.

Serum bilirubin levels were significantly higher when the subjects consumed the active bar than when they consumed the control bar (p=0.047). However, bilirubin was above 1.2 mg/dL, the upper limit of normal, in only 2 samples and these samples were hemolized (hemolysis is known to interfere with bilirubin determination).

Effect of bar supplementation on overall diet composition. As indicated above, the addition of the active bar to the diet lowered serum and LDL cholesterol. Diets were analyzed in order to determine whether the cholesterol-lowering effect was a direct result of the active bar or resulted from an alteration of the entire diet, and to determine whether either bar resulted in a net increase of calories to the diet relative to the baseline diet.

There was no statistically significant change in the components of the diet most likely to influence serum cholesterol levels independently of the active bar supplementation. As shown in Table 18, mean intakes of saturated fat, polyunsaturated fat, and cholesterol did not change significantly from period to period. Blood lipid changes were most likely directly caused by the active bar, not by a change of the overall diet in response to the addition of the active bar to the diet.

TABLE 18

DIETARY COMPONENTS LIKELY TO AFFECT SERUM CHOLESTEROL LEVELS (MEANS ± SEM)

|  | Saturated fat (% of calories) | Cholesterol (mg per day) | Polyunsaturated fat (% of calories) |
| --- | --- | --- | --- |
| Baseline | 11.6 ± 0.4 | 227 ± 20 | 6.5 ± 0.3 |
| Control | 11.5 ± 0.4 | 261 ± 19 | 7.2 ± 0.3 |
| Active | 11.9 ± 0.4 | 242 ± 23 | 7.0 ± 0.3 |

By virtue of their high content of dietary fiber and calcium, the active bars contributed positively to the total intake of dietary fiber and calcium. The mean intake of dietary fiber nearly doubled from a baseline intake of less than 15 g/day to levels of 27 g/day during the control period and 31 g/day during the active bar period (Table 19). The total intake of fiber was significantly higher during consumption of the active bar than the control bar as a result of slightly higher levels of fiber in the active bar than the control bar (see table). Mean calcium intake increased from a baseline intake of 933 mg/day to an mean intake of 1085 mg/day during the control period and 1,181 mg/day during the active bar period. Calcium intake was significantly higher during the active bar period than during the control bar period, even though calcium levels in the 2 bars were nearly identical. The small differences in total dietary fiber and calcium intake between the active and control bar periods cannot explain the substantial difference in serum cholesterol levels between the two periods.

The effect of supplementing the diet with two bars (either active or control) per day on total caloric intake was not statistically significant. Even though two bars contributed over 400 kcal per day to their diets, the subjects compensated their caloric intake, so that total caloric intake, like fat and cholesterol intake, were not measurably different during dietary intervention with either the control or active bars (Table 20). This was further verified by the absence of statistically significant weight changes at the end of the 3 weeks of dietary intervention (Table 20).

TABLE 19

DIETARY FIBER AND CALCIUM INTAKES

|  | Dietary Fiber (g/day) | Calcium (mg/day) |
| --- | --- | --- |
| Baseline | 14.6 ± 1.1 | 933 ± 76 |
| Control | 27.3 ± 0.9 | 1085 ± 43 |
| Active | 31.3 ± 1.0* | 1182 ± 51** |

*p = 0.003 (active vs. control)
**p = 0.01 (active vs. control)

TABLE 20

CALORIC INTAKE AND WEIGHT CHANGE

|  | Total Calories (kcal/day) | Weight (lbs) |
| --- | --- | --- |
| Baseline | 2333 ± 103 | 166.8 ± 4.8 |
| Control | 2360 ± 87 | 168.0 ± 4.8 |
| Active | 2319 ± 88 | 168.0 ± 4.7 |

Appetite/satiety evaluation. The present study recorded appetite prior to a meal and satiety following a meal once per week during the study according to the method of Haber et al., "Depletion and disruption of dietary fiber: effects on satiety, plasma glucose and serum insulin", THE LANCET, Oct. 1, 1977, pp. 679–682. The results indicate that ratings of appetite and satiety did not depend on which bar the subjects were eating at the time of evaluation. Furthermore, the subjects in the present study had the same total caloric intake with either bar as determined by the food records and maintained their weight exactly, which seems to indicate an overall lack of effect of guar in controlling appetite or food intake. Therefore, anecdotal information supporting the notion that the consumption of viscous fibers such as guar cause a feeling of satiety that translates into lower caloric intake were not supported by the present results.

Gastrointestinal Effects of the Active Bar. Several gastrointestinal effects were noted with the consumption of 2 active bars per day. Increased gas production (flatulence), larger stool numbers, and a softer stool consistency were the gastrointestinal parameters most obviously affected by the consumption of the active bars. We cannot determine from the present data to what extent these gastrointestinal effects would resolve over a longer term consumption of a high fiber diet. It is clear however that the gastrointestinal effects do resolve rapidly (within 1 to 2 days) by decreasing or ceasing the consumption of active bars.

Two subjects did drop out of the study, one as a result of heartburn and reflux and the other as a result of diarrhea (stool softness was significantly affected by the active bar as discussed above).

ADDITIONAL EMBODIMENTS

Several additional embodiments of nutritional products according to the invention, in the form of food bars, were manufactured in attempts to improve product texture, taste, and other aspects of the product.

A nutritional product in accordance with the present invention preferably contains a source of fat selected from the group consisting of vegetable oils containing, by weight, less than 25% saturated fatty acids. Examples of such vegetable oils are rice bran oil, canola oil, and corn oil.

A nutritional product in accordance with the present invention preferably contains soy protein, and may alternatively contain one or more protein sources selected from the group consisting of soy protein, oat protein and calcium caseinate.

A nutritional product in accordance with the invention may alternatively contain an acidulant in the solid matrix to stimulate salivation (to ease swallowing) or enhance flavor. Preferably the acidulant is selected from the group consisting of citric acid, malic acid, and fumeric acid. Citric acid has been used in several of the food bar prototypes.

FOOD BAR EXAMPLE 5

Food Bar Prototype Number 5 was an evaluation of the effect of using guar that had been more thickly encapsulated in combination with a soy protein system.

TABLE 21

RECIPE FOR FOOD BAR PROTOTYPE NUMBER 5

| INGREDIENT | CONCENTRATION BY PERCENT WEIGHT OF BAR |
|---|---|
| High Fructose Corn Syrup | 25.71 |
| Oat Bran[1] | 17.06 |
| Microencapsulated Guar[2] | 16.46 |
| Soy Protein | 11.44 |
| Rice Bran Oil[3] | 10.13 |
| Polydextrose | 6.62 |
| Glycerin | 6.18 |
| Rice Crisp | 4.45 |
| Dicalcium Phosphate | 0.97 |
| Lecithin | 0.59 |
| Citric Acid | 0.39 |

[1]The "oat bran" used was actually a mixture comprising, by weight, 26.25% oat fiber, 62.128% oat flour and 11.622% soy protein.
[2]The guar gum was encapsulated as described above in ENCAPSULATION EXPERIMENT 14.
[3]Physically refined rice bran oil from Tsuno Rice Fine Chemical Co., Wakayama, Japan Manufacturing Procedure:

Food Bar Prototype Number 5 was prepared in a Hobart mixer. All ingredients were added to the mixer and mixed at room temperature (24°±10° C.). The first ingredients placed in the mixer were the soy protein, dicalcium phosphate, and citric acid which were mixed until blended. The rice bran oil, and lecithin were then added and mixed until blended. The zein microencapsulated guar was then added and mixed until blended. The polydextrose, oat bran and crisp rice, were then added and mixed until blended. The final ingredients added to the mixer were the high fructose corn syrup, and glycerin which were and mixed with the other ingredients until blended. The batch was then dumped on to the bench top and rolled out using a typical rolling pin to a uniform thickness. The batch was cut into bars with a spatula then cooled in a refrigerator to between 0° and 10° C. At no time were the food bars subjected to elevated temperatures for baking. Of course friction due to mixing could elevate the temperature of the blend several degrees. The bars were then packaged in a low density polyethylene/foil wrap.

The texture of the prototype food bars was determined several times over a period of weeks using the method described above in Food Bar Example 1, and the results are presented in TABLE 22.

TABLE 22

TEXTURE TESTING FOR FOOD BAR PROTOTYPE NUMBER 5

| WEEK | FOOD BAR HARDNESS |
|---|---|
| 0 | 44 |
| 2 | 164 |
| 4 | 227 |
| 6 | 262 |
| 8 | 349 |
| 16 | 516 |

These test results indicated that even with better encapsulation of guar, food bar texture (hardness) might still be improved by employing a different protein system.

FOOD BAR EXAMPLE 6

Food Bar Prototype Number 6 was manufactured to evaluate the use of calcium caseinate as a protein system because the results of FOOD BAR EXAMPLE 5 indicated that soy protein may contribute to a hard bar texture.

TABLE 23

RECIPE FOR FOOD BAR PROTOTYPE NUMBER 6

| INGRIEDIENT | CONCENTRATION BY PERCENT WEIGHT OF BAR |
|---|---|
| High Fructose Corn Syrup | 23.23 |
| Oat Bran[1] | 18.32 |
| Microencapsulated Guar[2] | 16.70 |
| Calcium Caseinate | 11.61 |
| Rice Bran Oil[3] | 10.28 |
| Polydextrose | 6.72 |
| Glycerin | 6.57 |
| Crisp Rice | 4.52 |
| Dicalcium Phosphate | 0.99 |
| Lecithin | 0.60 |
| Citric Acid | 0.40 |
| Flavor (Raspberry) | 0.06 |

[1]The "oat bran" used was actually a mixture comprising, by weight, 26.25% oat fiber, 52.128% oat flour and 11.622% soy protein.
[2]The guar gum was encapsulated as described above in ENCAPSULATION EXPERIMENT 14.
[3]Physically refined rice bran oil from Tsuno Rice Fine Chemical Co., Wakayama, Japan.

Manufacturing Procedure:

Food Bar Prototype Number 6 was prepared in a Hobart mixer. All ingredients were added to the mixer and mixed at room temperature (24°±10° C.). The first ingredients placed in the mixer were the calcium caseinate, dicalcium phosphate, and citric acid and mixed until blended. The rice bran oil, flavor and lecithin were then added and mixed until blended. The microencapsulated guar was then added and mixed until blended. The polydextrose, oat bran, and crisp rice were then added and mixed until blended. The high fructose corn syrup and glycerin were then added and mixed until blended. The batch was then dumped onto the bench top and rolled out using a typical rolling pin to a uniform thickness. The batch was cut into bars with a spatula then cooled in a refrigerator to between 0° and 10° C. At no time were the food bars subjected to elevated temperatures for baking. Of course friction due to mixing could elevate the temperature of the blend several degrees. The bars were then packaged in a low density polyethylene/foil wrap.

The texture of these prototype food bars was determined several times over a period of weeks using the method described above in Food Bar Example 1, and the results are presented in TABLE 24.

TABLE 24

TEXTURE TESTING FOR FOOD BAR PROTOTYPE NUMBER 6

| WEEK | FOOD BAR HARDNESS |
|---|---|
| 0 | 17 |
| 2 | 57 |
| 4 | 98 |
| 6 | 142 |
| 8 | 169 |
| 10 | 157 |
| 16 | 225 |
| 24 | 253 |

These test results indicated that a calcium caseinate protein system is beneficial for improving food bar texture (hardness).

FOOD BAR EXAMPLE 7

Food Bar Prototype Number 7 was manufactured to evaluate a protein system comprising, by weight, 60% soy protein and 40% calcium caseinate. It is believed to be desirable to have soy protein in the protein system because it is theorized that soy protein may contribute to a reduction in serum cholesterol.

TABLE 25

RECIPE FOR FOOD BAR PROTOTYPE NUMBER 7

| INGREDIENT | CONCENTRATION BY PERCENT WEIGHT OF BAR |
|---|---|
| High Fructose Corn Syrup | 25.71 |
| Oat Bran[1] | 17.06 |
| Microencapsulated Guar[2] | 16.46 |
| Rice Bran Oil[3] | 10.13 |
| Soy Protein | 6.86 |
| Polydextrose | 6.62 |
| Glycerin | 6.18 |
| Calcium Caseinate | 4.58 |
| Crisp Rice | 4.45 |
| Dicalcium Phosphate | 0.97 |
| Lecithin | 0.59 |
| Citric Acid | 0.39 |

[1] The "oat bran" used was actually a mixture comprising, by weight, 26.25% oat fiber, 62.128% oat flour and 11.622% soy protein
[2] The guar gum was encapsulated as described above in ENCAPSULATION EXPERIMENT 14.
[3] Physically refined rice bran oil from Tsuno Rice Fine Chemical Col., Wakayama, Japan.

Manufacturing Procedure:

Food Bar Prototype Number 7 was prepared in a Hobart mixer. All ingredients were added to the mixture and mixed at room temperature (24°±10° C.). The first ingredients added to the mixer were the soy protein, calcium caseinate, dicalcium phosphate, and citric acid which were mixed until blended. The rice bran oil, and lecithin were then added and mixed until blended. The zein microencapsulated guar was then added and mixed until blended. The polydextrose, oat bran, and crisp rice, were then added and mixed with the other ingredients until blended. The final ingredients added to the mixer were the high fructose corn syrup, and glycerin and mixed until blended. The batch was then dumped on to the bench top and rolled out using a typical rolling pin to a uniform thickness. The batch was cut into bars with a spatula then cooled in a refrigerator to between 0° and 10° C. At no time were the food bars subjected to elevated temperatures for baking. Of course friction due to mixing could elevate the temperature of the blend several degrees. The bars were then packaged in a low density polyethylene/foil wrap.

The texture of the prototype food bars was determined several times over a period of weeks using the method described above in Food Bar Example 1, and the results are presented in TABLE 26.

TABLE 26

TEXTURE TESTING FOR FOOD BAR PROTOTYPE NUMBER 7

| WEEK | FOOD BAR HARDNESS |
|---|---|
| 0 | 30 |
| 2 | 86 |
| 4 | 163 |
| 6 | 187 |
| 8 | 190 |
| 16 | 305 |
| 24 | 343 |

These test results indicated that a protein system that is a blend of soy protein and calcium caseinate has a positive effect on food bar texture (hardness) as compared to a protein system that is 100% soy protein.

FOOD BAR EXAMPLE 8

Food Bar Prototype Number 8 was manufactured to evaluate a protein system comprising, by weight, 60% soy protein and 40% whey protein isolate.

TABLE 27

RECIPE FOR FOOD BAR PROTOTYPE NUMBER 8

| INGREDIENT | CONCENTRATION BY PERCENT WEIGHT OF BAR |
|---|---|
| High Fructose Corn Syrup | 25.71 |
| Oat Bran[1] | 17.06 |
| Microencapsulated Guar[2] | 16.46 |
| Rice Bran Oil[3] | 10.13 |
| Soy Protein | 6.86 |
| Polydextrose | 6.62 |
| Glycerin | 6.18 |
| Whey Protein Isolate | 4.58 |
| Crisp Rice | 4.45 |
| Dicalcium Phosphate | 0.97 |
| Lecithin | 0.59 |
| Citric Acid | 0.39 |

[1] The "oat bran" used was actually a mixture comprising, by weight, 26.25% oat fiber, 62.128% oat flour and 11.622% soy protein
[2] The guar gum was encapsulated as described above in ENCAPSULATION EXPERIMENT 14.
[3] Physically refined rice bran oil from Tsuno Rice Fine Chemical Co., Wakayama, Japan.

Manufacturing Procedure:

Food Bar Prototype Number 8 was prepared in a Hobart mixer. All ingredients were added to the mixture and mixed at room temperature (24°±10° C.). The first ingredients added to the mixer were the whey protein isolate, soy protein, dicalcium phosphate, and citric acid which were mixed until blended. The rice bran oil, and lecithin were then added and mixed until blended. The zein microencapsulated guar was then added and mixed until blended. The polydextrose, oat bran, and crisp rice, were then added and mixed until blended. The final ingredients added to the mixer were the high fructose corn syrup, and glycerin which were mixed with the other ingredients until blended. The batch was then dumped on to the bench top and rolled out using a typical rolling pin to a uniform thickness. The batch was cut into bars with a spatula then cooled in a refrigerator to between 0° and 10° C. At no time were the food bars subjected to elevated temperatures for baking. Of course friction due to mixing could elevate the temperature of the blend a few degrees. The bars were then packaged in a low density polyethylene/foil wrap.

The texture of the prototype food bars was determined over a period of weeks using the method described above in Food Bar Example 1, and the results are presented in TABLE 28.

TABLE 28

TEXTURE TESTING FOR FOOD BAR PROTOTYPE NUMBER 8

| WEEK | FOOD BAR HARDNESS |
|---|---|
| 0 | 27 |
| 2 | 174 |
| 4 | 160 |
| 6 | 152 |
| 8 | 250 |
| 16 | 312 |

These test results indicated that a protein system that is a blend of soy protein and whey protein isolate has a positive effect on food bar texture (hardness) as compared to a protein system that is 100% soy protein.

FOOD BAR EXAMPLE 9

In order to slow down bar hardening and drying, Food Bar Prototype Number 9 was developed. A significant reduction in the amount of oat bran and the addition of maltodextrin and honey appears to have improved bar physical characteristics.

TABLE 29

RECIPE FOR FOOD BAR PROTOTYPE NUMBER 9

| INGREDIENT | CONCENTRATION BY PERCENT WEIGHT OF BAR |
|---|---|
| High Fructose Corn Syrup | 23.64 |
| Microencapsulated Guar[1] | 16.62 |
| Rice Bran Oil[2] | 10.24 |
| Oat Bran[3] | 8.62 |
| Maltodextrin | 8.62 |
| Soy Protein | 6.93 |
| Polydextrose | 6.69 |
| Glycerin | 6.24 |
| Calcium Caseinate | 4.62 |
| Crisp Rice | 4.50 |
| Honey | 1.30 |
| Dicalcium Phosphate | 0.98 |
| Lecithin | 0.60 |
| Citric Acid | 0.40 |

[1]The guar gum was encapsulated as described above in ENCAPSULATION EXPERIMENT 14.
[2]Physically refined rice bran oil from Tsuno Rice Fine Chemical Co., Wakayama, Japan.
[3]The "oat bran" used was actually a mixture comprising, by weight, 26.25% oat fiber, 62.128% oat flour and 11.622% soy protein.

Manufacturing Procedure:

Food Bar Prototype Number 9 was prepared in a Hobart mixer. The first ingredients added to the mixer were the soy protein, calcium caseinate, dicalcium phosphate, and citric acid and mixed until blended. The rice bran oil, and lecithin were then added to the mixer and mixed until blended. The zein microencapsulated guar was then added and mixed until blended. The polydextrose, maltodextrin, oat bran, and crisp rice, were then added and mixed until blended. The final ingredients added to the mixer were the high fructose corn syrup, honey and glycerin which were mixed with the other ingredients until blended. The batch was then dumped on to the bench top and rolled out using a typical rolling pin to a uniform thickness. The batch was cut into bars with a spatula then cooled in a refrigerator to between 0° and 10° C. At no time were the food bars subjected to elevated temperatures for baking. Of course, friction due to mixing could elevate the temperature of the blend a few degrees. The bars were then packaged in a low density polyethylene/foil wrap. The texture of these prototype food bars was determined several times over a period of weeks using the method described above in Food Bar Example 1, and the results are presented in TABLE 30.

TABLE 30

TEXTURE TESTING FOR FOOD BAR PROTOTYPE NUMBER 9

| WEEK | FOOD BAR HARDNESS |
|---|---|
| 0 | 12 |
| 2 | 13 |
| 4 | 15 |
| 6 | 22 |
| 8 | 29 |
| 16 | 30 |

FOOD BAR EXAMPLE 10

To enhance bar appearance a low fat confectionery coating was applied. Less than 30 percent of the calories in this bar prototype come from fat.

TABLE 31

RECIPE FOR FOOD BAR PROTOTYPE NUMBER 10

| INGREDIENT | CONCENTRATION BY PERCENT WEIGHT OF BAR |
|---|---|
| High Fructose Corn Syrup | 23.12 |
| Microencapsulated Guar[1] | 16.69 |
| Confectionery Coating | 15.30 |
| Oat Bran[2] | 6.01 |
| Maltodextrin | 5.59 |
| Soy Protein | 5.51 |
| Glycerin | 5.00 |
| Polydextrose | 4.49 |
| Rice Bran Oil[3] | 4.74 |
| Mineral Premix | 4.32 |
| Calcium Caseinate | 3.64 |
| Rice Crisp | 3.56 |
| Honey | 1.02 |
| Lecithin | 0.51 |
| Graham Cracker Flavor | 0.25 |
| Graham Flavor | 0.17 |
| Creamy Vanilla Flavor | 0.08 |

[1]The guar gum was encapsulated as described above in ENCAPSULATION EXPERIMENT 14.
[2]The "oat bran" used was actually a mixture comprising by weight, 26-25% oat fiber, 62.128% oat flour and 11.622% soy protein
[3]Chemically refined Rice Bran Oil from Riceland Foods, Inc., Stuttgart, Arkansas.

Manufacturing Procedure:

Food Bar Prototype Number 10 was prepared in a kneader. The first ingredients added to the kneader were the soy protein, calcium caseinate, and mineral premix and mixed until blended. The rice bran oil, lecithin, graham cracker flavor, graham flavor and creamy vanilla flavor were then added to the kneader and mixed until blended. The zein microencapsulated guar was then added and mixed until blended. The polydextrose, maltodextrin, oat bran, and crisp rice, were then added and mixed until blended. The final ingredients added to the mixer were the high fructose corn syrup, honey and glycerin and mixed until blended. The batch was then extruded and cut into bars by a extruder/ cutter. The bars were then coated with the confectionery coating with a coating system. At no time were the food bars subjected to elevated temperatures for baking. Of course, friction due to mixing could elevate the temperature of the blend a few degrees. The bars were then packaged in a low density polyethylene/foil wrap.

The texture of these prototype food bars was determined several times over a period of weeks using the method described in Food Bar Example 1, and the results are presented in TABLE 32.

TABLE 32

TEXTURE TESTING FOR FOOD BAR PROTOTYPE NUMBER 10

| WEEK | FOOD BAR HARDNESS |
|---|---|
| 0 | 61 |
| 2 | 181 |

FOOD BAR EXAMPLE 11

Food Bar Prototype Number 11 was manufactured in order to enhance gastrointestinal tolerance by reducing the amount of encapsulated guar. To maintain at least seven grams of fiber in the food bar, barley meal and soy polysaccharide were added.

TABLE 33

RECIPE FOR FOOD BAR PROTOTYPE NUMBER 11

| INGREDIENT | CONCENTRATION BY PERCENT WEIGHT OF BAR |
|---|---|
| High Fructose Corn Syrup | 23.72 |
| Microencapsulated Guar[1] | 11.17 |
| Barley Meal[2] | 10.17 |
| Rice Bran Oil[3] | 9.48 |
| Soy Protein | 6.78 |
| Glycerin | 6.10 |
| Polydextrose | 5.49 |
| Mineral Premix | 5.19 |
| Maltodextrin | 4.99 |
| Calcium Caseinate | 4.48 |
| Rice Crisp | 4.39 |
| Oat Bran[4] | 3.79 |
| Soy Polysaccharide | 1.70 |
| Honey | 1.30 |
| Lecithin | 0.60 |
| Graham Cracker Flavor | 0.32 |
| Graham Flavor | 0.21 |
| Creamy Vanilla Flavor | 0.12 |

[1]The guar gum was encapsulated as described above in ENCAPSULATION EXPERIMENT 14.
[2]Prowashnupana Whole Grain Barley Meal
[3]Chemically refined Rice Bran Oil from Riceland Foods Inc. Stuttgart, Arkansas
[4]Oat Bran from Quaker Oats Chicago, IL Manufacturing Procedure:

Food Bar Prototype Number 11 was prepared in a Hobart mixer. The first ingredients added to the mixer were the soy protein, calcium caseinate, and mineral premix and mixed until blended. The rice bran oil, lecithin, graham cracker flavor, graham flavor and creamy vanilla flavor were then added to the mixer and mixed until blended. The zein microencapsulated guar was then added and mixed until blended. The polydextrose, maltodextrin, oat bran, barley meal, soy polysaccharide and crisp rice, were then added and mixed until blended. The final ingredients added to the mixer were the high fructose corn syrup, honey and glycerin and mixed until blended. The batch was then dumped on to the bench top and rolled out using a typical rolling pin to a uniform thickness. The batch was cut into bars with a spatula then cooled in a refrigerator to between 0° and 10° C. At no time were the food bars subjected to elevated temperatures for baking. Of course, friction due to mixing could elevate the temperature of the blend a few degrees. The bars were then packaged in a low density polyethylene/foil wrap.

The texture of this prototype food bar was determined only at the time of manufacture using the method described above in Food Bar Example 1. At the time of manufacture the food bar hardness was 37.

ALTERNATIVE SOY PROTEIN SOURCES

The soy protein used in each of the food bar prototypes described above was SUPRO® 1610 (formerly called PP 1610) which is a commercially available soy protein isolate manufactured by Protein Technology International which is a division of Ralston Purina, 835 South 8th Street, St. Louis, Mo. 63012, U.S.A. In attempts to evaluate the effect of the soy protein on product texture other commercially available soy protein sources were substituted for the SUPRO® 1610. SUPRO® 661, which is also manufactured by Protein Technology International, has been found to be a superior soy protein source with respect to product texture. A person of ordinary skill in the art may select a protein source that imparts the desired nutritional and texture qualities to a nutritional product in accordance with the present invention.

The nutritional profile of a food bar in accordance with preferred embodiments of the present invention is presented in TABLE 34.

TABLE 34

NUTRITIONAL PROFILE OF A FOOD BAR ACCORDING TO PREFERRRED EMBODIMENTS

| | |
|---|---|
| Told Calories | 130–170 kcals/bar |
| Caloric Distribution (as % of total calories) | |
| Protein | 15–20% |
| Carbohydrate | 52–61% |
| Fat | 24–28% |
| ANTI-OXIDANTS | |
| β-carotene | minimum of 1,338 IU (2.5 mg) |
| Tocopherols all natural RRR-α-tocopherol) | minimum of 250 IU |
| Selenium | minimum of 30 µg |
| Ascorbate | minimum of 300 mg |

| OTHER NUTRIENTS | MINIMUM | TARGET |
|---|---|---|
| Vitamin D, IU | 50 | 60 |
| Vitamin K, mcg | 10 | 12 |
| Folic Acid, mcg | 50 | 60 |
| Thiamin, mg | 0.19 | 0.23 |
| Riboflavin, mg | 0.22 | 0.26 |
| Vitamin $B_6$, mg | 0.25 | 0.30 |
| Vitamin $B_{12}$, mcg | 0.75 | 0.90 |
| Niacin, mg | 2.50 | 3.00 |
| Biotin, mcg | 37.5 | 45 |
| Pantothenic acid, mg | 1.25 | 1.5 |
| Sodium, mg | 145 | 174 |
| Potassium, mg | 250 | 300 |
| Chloride, mg | 190 | 228 |
| Calcium, mg | 125 | 150 |
| Phosphorus, mg | 125 | 150 |
| Magnesium, mg | 50 | 60 |
| Iodine, mcg | 19 | 22.8 |

TABLE 34-continued

NUTRITIONAL PROFILE OF A FOOD BAR ACCORDING TO PREFERRRED EMBODIMENTS

| | | |
|---|---|---|
| Manganese, mg | 0.65 | 0.78 |
| Copper, mg | 0.25 | 0.30 |
| Zinc, mg | 2.82 | 3.38 |
| Iron, mg | 2.25 | 2.70 |
| Chromium, mcg | 12.5 | 15 |
| Molybdenum, mcg | 19 | 22.8 |
| Carnitine, mg | 25 | 25 |
| Taurine, mg | 25 | 25 |

We claim:

1. A nutritional product comprising a solid matrix comprising fat, carbohydrate, and at least one protein selected from the group consisting of vegetable proteins and milk proteins, said solid matrix having dispersed therein particles comprising a dietary fiber which lowers Serum cholesterol in humans encapsulated in zein.

2. A nutritional product according to claim 1 wherein the dietary fiber is guar.

3. A nutritional product according to claim 1 wherein said particles comprise guar encapsulated in about 20% add-on zein.

4. A nutritional product according to any one of claims 1–3 wherein a source of protein is soy protein.

5. A nutritional product according to any one of claims 1–3 wherein a source of fat is selected from the group consisting of vegetable oils containing, by weight, less than 25% saturated fatty acids.

6. A nutritional product according to any one of claims 1–3 wherein the protein is soy protein and the fat is selected from the group consisting of vegetable oils containing, by weight, less than 25% saturated fatty acids.

7. A nutritional product according to any one of claims 1–3 wherein the protein is soy protein and oat protein.

8. A nutritional product according to any one of claims 1–3 wherein the protein is soy protein and calcium caseinate.

9. A nutritional product according to any one of claims 1–3 wherein the protein is soy protein, oat protein and calcium caseinate.

10. A nutritional product for lowering serum cholesterol in humans comprising a solid matrix comprising fat, carbohydrate, at least one protein selected from the group consisting of vegetable proteins and milk proteins, and vitamins and minerals, said solid matrix having dispersed therein a serum cholesterol reducing quantity of particles comprising guar encapsulated in zein.

11. A nutritional product according to claim 10 wherein the protein is soy protein.

12. A nutritional product according to claim 10 wherein the fat is selected from the group consisting of vegetable oils containing, by weight, less than 25% saturated fatty acids.

13. A nutritional product according to claim 11 wherein the fat is selected from the group consisting of vegetable oils containing, by weight, less than 25% saturated fatty acids.

14. A nutritional product for lowering serum cholesterol in humans comprising a solid matrix of soy protein, rice bran oil, and carbohydrate, said solid matrix having dispersed therein a serum cholesterol reducing quantity of particles comprising guar encapsulated in zein.

15. A nutritional product according to claim 14 wherein said particles comprise guar encapsulated by at least about 20% add-on zein.

16. A nutritional product according to claim 14 wherein said solid matrix further comprises oat protein.

17. A nutritional product according to claim 14 wherein said solid matrix further comprises calcium caseinate.

18. A nutritional product according to claim 14 wherein said solid matrix further comprises calcium caseinate and oat protein.

19. A nutritional product according to claim 14 wherein the solid matrix further comprises an acidulant selected from the group consisting of citric acid, malic acid, and fumeric acid.

* * * * *